US007015816B2

(12) United States Patent
Wildman et al.

(10) Patent No.: US 7,015,816 B2
(45) Date of Patent: Mar. 21, 2006

(54) HYGIENE MONITORING SYSTEM

(75) Inventors: Timothy D. Wildman, Metamora, IN (US); Dennis J. Gallant, Harrison, OH (US); Phill Hausman, Cary, NC (US)

(73) Assignee: Hill-Rom Services, Inc., Wilmington, DE (US)

( * ) Notice: Subject to any disclaimer, the term of this patent is extended or adjusted under 35 U.S.C. 154(b) by 29 days.

(21) Appl. No.: 10/698,652

(22) Filed: Oct. 31, 2003

(65) Prior Publication Data
US 2004/0090333 A1 May 13, 2004

Related U.S. Application Data

(63) Continuation of application No. 09/699,796, filed on Oct. 30, 2000, now Pat. No. 6,727,818.

(60) Provisional application No. 60/223,365, filed on Aug. 7, 2000, provisional application No. 60/169,315, filed on Dec. 7, 1999, provisional application No. 60/162,537, filed on Oct. 29, 1999.

(51) Int. Cl.
G08B 13/14 (2006.01)

(52) U.S. Cl. ............................... 340/573.1; 340/539.1; 340/539.11; 340/572.1

(58) Field of Classification Search ............. 340/573.1, 340/539.1, 539.11, 572.1
See application file for complete search history.

(56) References Cited

U.S. PATENT DOCUMENTS

| 4,275,385 A | 6/1981 | White |
|---|---|---|
| 4,601,064 A | 7/1986 | Shipley |
| 5,016,172 A | 5/1991 | Dessertine |
| 5,119,104 A | 6/1992 | Heller |
| 5,199,118 A | 4/1993 | Cole et al. |
| 5,202,666 A | 4/1993 | Knippscheer |
| 5,291,399 A | 3/1994 | Chaco |
| 5,387,993 A | 2/1995 | Heller et al. |
| RE35,035 E | 9/1995 | Shipley |
| 5,455,851 A | 10/1995 | Chaco et al. |
| 5,465,082 A | 11/1995 | Chaco |
| 5,515,426 A | 5/1996 | Yacenda et al. |
| 5,548,637 A | 8/1996 | Heller et al. |
| 5,561,412 A | 10/1996 | Novak et al. |
| 5,572,195 A | 11/1996 | Heller et al. |
| 5,594,786 A | 1/1997 | Chaco et al. |
| 5,610,589 A | 3/1997 | Evans et al. |
| 5,633,742 A | 5/1997 | Shipley |
| 5,670,945 A | 9/1997 | Applonie |
| 5,689,229 A | 11/1997 | Chaco et al. |
| 5,695,091 A | 12/1997 | Winings et al. |
| 5,699,038 A | 12/1997 | Ulrich et al. |
| 5,702,115 A | 12/1997 | Pool |
| 5,745,272 A | 4/1998 | Shipley |
| 5,774,865 A | 6/1998 | Glynn |
| 5,781,942 A | 7/1998 | Allen et al. |
| 5,793,653 A | 8/1998 | Segal |
| 5,812,059 A | 9/1998 | Shaw et al. |
| 5,818,617 A | 10/1998 | Shipley |
| 5,822,418 A | 10/1998 | Yacenda et al. |
| 5,822,544 A | 10/1998 | Chaco et al. |
| 5,838,223 A | 11/1998 | Gallant et al. |
| 5,900,067 A | 5/1999 | Jones |

(Continued)

FOREIGN PATENT DOCUMENTS

DE 19903079 A 1 8/2000

*Primary Examiner*—Julie Bichngoc Lieu
(74) *Attorney, Agent, or Firm*—Bose McKinney & Evans LLP

(57) ABSTRACT

A method is provided for monitoring hygiene compliance.

30 Claims, 13 Drawing Sheets

U.S. PATENT DOCUMENTS

| | | |
|---|---|---|
| 5,900,801 A | 5/1999 | Heagle et al. |
| 5,939,974 A | 8/1999 | Heagle et al. |
| 5,945,910 A | 8/1999 | Gorra |
| 5,952,924 A | 9/1999 | Evans et al. |
| 5,954,069 A | 9/1999 | Foster |
| 5,966,753 A | 10/1999 | Gauthier et al. |
| 6,038,331 A | 3/2000 | Johnson |
| 6,125,482 A | 10/2000 | Foster |
| 6,147,607 A | 11/2000 | Lynn |
| 6,195,588 B1 | 2/2001 | Gauthier et al. |
| 6,211,788 B1 | 4/2001 | Lynn et al. |
| 6,236,317 B1 | 5/2001 | Cohen et al. |

REPORT #1

HOSPITAL SUMMARY REPORT
Time Period: 10/01/99 to 11/01/99
Compliance Rating: 80%

| Dept | Visitations | Compliance |
|---|---|---|
| CCU | 2000 | 73% |
| MedSurg | 5000 | 40% |
| ICU | 1500 | 70% |
| CVICU | 1000 | 85% |

Hospital Summary Report: Will give a summary of the compliance to handwashing guidelines for the Hospital and specific department within a healthcare environment. The purpose of the report is to identify Departments within the Hospital who have the most difficulty with compliance so that corrective action can be taken.

FIG. 10

REPORT #2

DEPARTMENT SUMMARY REPORT
Dept: Critical Care Unit 52
Time Period: 10/01/99 to 11/01/99
Dept. Compliance Rating: 73%

| Location | Visitations | Compliance |
|---|---|---|
| 201 | 350 | 80% |
| 203 | 540 | 80% |
| 205 | 350 | 50% |
| 206 | 540 | 80% |
| 207 | 350 | 90% |

Department Summary Report: Will give a summary of the compliance to handwashing guidelines for a specific department within a healthcare environment.
The purpose of the report is to identify area within the unit and groups of caregivers who have the most difficulty with compliance so that corrective action can be taken.

Number of times caregivers entered into a zone where handwashing was required

| ID | Group | Visitations | Compliance |
|---|---|---|---|
| 0100 | Visiting Physicians | 1350 | 50% |
| 0200 | Nursing | 5500 | 95% |
| 0300 | Visitors | 550 | 50% |

This section allows quick indentification of each groups contributions to the overall compliance rating

FIG. 11

REPORT #3

GROUP SUMMARY REPORT
Dept: Critical Care Unit 52
Group: Visiting Physician
Time Period: 10/01/99 to 11/01/99
Dept. Compliance Rating: 50%

| Location | Visitations | Compliance |
|---|---|---|
| 201 | 300 | 25% |
| 203 | 200 | 75% |
| 205 | 500 | 50% |
| 206 | 200 | 80% |
| 207 | 150 | 30% |

Group Summary Report: Will give a summary of the compliance to handwashing guidelines for a specific group of caregivers within a healthcare environment. The purpose of the report is to identify area within the Unit where with compliance is lowest so that corrective action can be taken with a specific Group of caregivers

| ID | Group | Visitations | Compliance |
|---|---|---|---|
| 0001 | Dr. Jon Smith | 100 | 56% |
| 0002 | Dr. Marry Jones | 200 | 93% |
| 0003 | Dr. Timothy D. Wildman | 550 | 38% |
| 0004 | Dr. Dennis Gallant | 500 | 45% |

This section allows quick indentification of each Individual's contribution to the Group's overall compliance rating

FIG. 12

REPORT #4

INDIVIDUAL SUMMARY REPORT
ID: 012345
Person: Dr. Jon Smith
Dept. Critical Care Unit 52
Group: Visiting Physican
Time Period: 10/01/99 to 11/01/99
Dept. Compliance Rating: 56%

| Location | Visitations | Compliance |
|----------|-------------|------------|
| 201 | 10 | 10% |
| 203 | 30 | |
| 205 | 5 | 30% |
| 206 | 20 | 60% |
| 207 | 15 | 20% |

Individual Summary Report: Will give a summary of the compliance to handwashing guidelines for a specific individual within a healthcare environment. The purpose of the report is to identify area within the unit where an individual may be having the most difficulty with compliance so that corrective action can be taken.

Each zone within Department or Hospital will be given a specific indentification number such that an understanding to where the infractions can be captured.

FIG. 13A

REPORT #4

INDIVIDUAL DETAILED COMPLIANCE REPORT
ID: 012345
Person: Dr. Jon Smith
Dept. Critical Care Unit 52
Group: Visiting Physican
Time Period: 10/01/99 11:30 to 13:45
Compliance Rating: 80%

| Location | Time | Status |
|----------|------|--------|
| 201 | 11:35 | Verified |
| 203 | 11:50 | Verified |
| 205 | 12:11 | Verified |
| 206 | 12:15 | Incomplete |
| 207 | 12:42 | Verified |

Individual Detailed Compliance Report: Will give a summary of the compliance to handwashing guidelines fo a specific individual over a specific time frame within a healthcare environment. The purpose of the report is to understand traffic patterns of an individual to that greater insight as to why compliance is not occurring can be gained.

FIG. 13B

HYGIENE MONITORING SYSTEM

REFERENCE TO OTHER APPLICATIONS

This application is a continuation of U.S. application Ser. No. 09/699,796 filed Oct. 30, 2000, now U.S. Pat. No. 6,727,818, which claims the benefit of U.S. Provisional Application No. 60/162,537 filed Oct. 29, 1999, the disclosures of both of which are hereby incorporated by reference; U.S. Provisional Application No. 60/169,315, filed Dec. 7, 1999, the disclosure of which is hereby incorporated by reference; and U.S. Provisional Application No. 60/223,365, filed Aug. 7, 2000, the disclosure of which is hereby incorporated by reference.

TECHNICAL FIELD OF THE INVENTION

The present invention relates to a system for monitoring compliance with hygiene policies.

BACKGROUND OF THE INVENTION

Systems to promote hygiene have been used in the healthcare industries as well as the food processing and preparation industries. See for example, U.S. Pat. No. 6,125,482, U.S. Pat. No. 6,038,331, U.S. Pat. No. 5,966,573, U.S. Pat. No. 5,952,924, U.S. Pat. No. 5,954,069, U.S. Pat. No. 5,945,910, U.S. Pat. No. 5,939,974, U.S. Pat. No. 5,900,801, U.S. Pat. No. 5,812,059, U.S. Pat. No. 5,793,653, U.S. Pat. No. 5,781,942, U.S. Pat. No. 5,610,589, U.S. Pat. No. 5,202,666, and U.S. Pat. No. 5,199,118.

SUMMARY OF THE INVENTION

Hygiene monitoring systems, which incorporate various features of the present invention, monitor location of persons in a facility, location of equipment in the facility, activities performed by persons in the facility, activities performed by equipment in the facility, and/or activities performed on equipment in the facility. From such gathered information, the hygiene monitoring systems determine whether certain actions (e.g. washing of a person's hands, washing of a piece of equipment) need to take place in order to comply with a hygiene policy defined for the facility. The hygiene monitoring systems may evaluate level of compliance with the hygiene policy, and provide persons with information (e.g. alerts, reminders, etc.) which aid in increasing the level of compliance with the hygiene policy.

BRIEF DESCRIPTION OF THE DRAWINGS

FIG. 10 shows a sample hospital summary compliance report;

FIG. 11 shows a sample department summary compliance report;

FIG. 12 shows a sample group summary compliance report;

FIG. 13A shows a sample individual summary compliance report;

FIG. 13B shows a sample individual detailed compliance report; and

DETAILED DESCRIPTION OF EXEMPLARY OF THE PRESENT INVENTION

Figure 1:
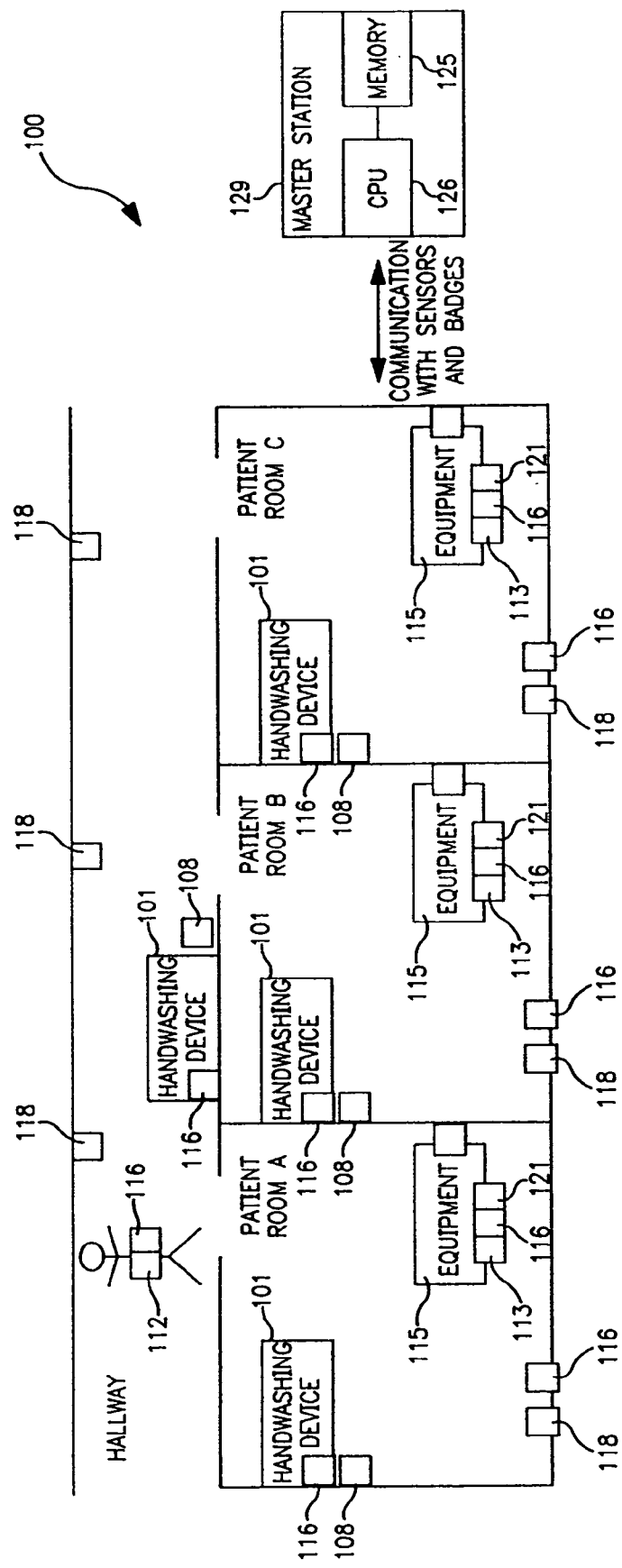
FIG. 1 shows a block diagram of a hygiene monitoring system which incorporates various features of the present invention therein.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Hygiene Monitoring System Architecture

FIGS. 1–4 illustrate an exemplary hygiene monitoring system 100 which incorporates various features of the present invention therein. In general, the hygiene monitoring system 100 is operable to monitor compliance with a particular hygiene policy defined for a facility. To this end, the exemplary hygiene monitoring system 100 includes handwashing devices 101, sensors 108 associated with the handwashing devices 101, caregiver badges 112, equipment badges 113 for monitoring equipment 115, alert indicators 116, sensors 118 operable to communicate with caregiver badges 112 and equipment badges 113, usage sensors 119 associated with monitored equipment 115, cleaning sensors 121 associated with monitored equipment 115, and a master station 129.

The master station 129 includes memory 125, a processing unit 126 and software stored in the memory 125. The software when executed by the processing unit 126 generally causes the master station 129 to monitor persons and equipment within the facility to monitor compliance with a hygiene policy defined for the facility. More specifically the master station 129 is operable to generate a compliance report 128 based upon the processing of data by the central processing unit 126. Examples of compliance reports are shown in FIGS. 4, 10–12, 13A, 13B, and 14. Further, the master station 129 may be hardwired to the sensors 108, 118, 119, 121 in order to receive and/or transmit information therebetween. Alternatively, the master station 129 may communicate wirelessly with the sensors 108, 118, 119, 121.

Figure 2:
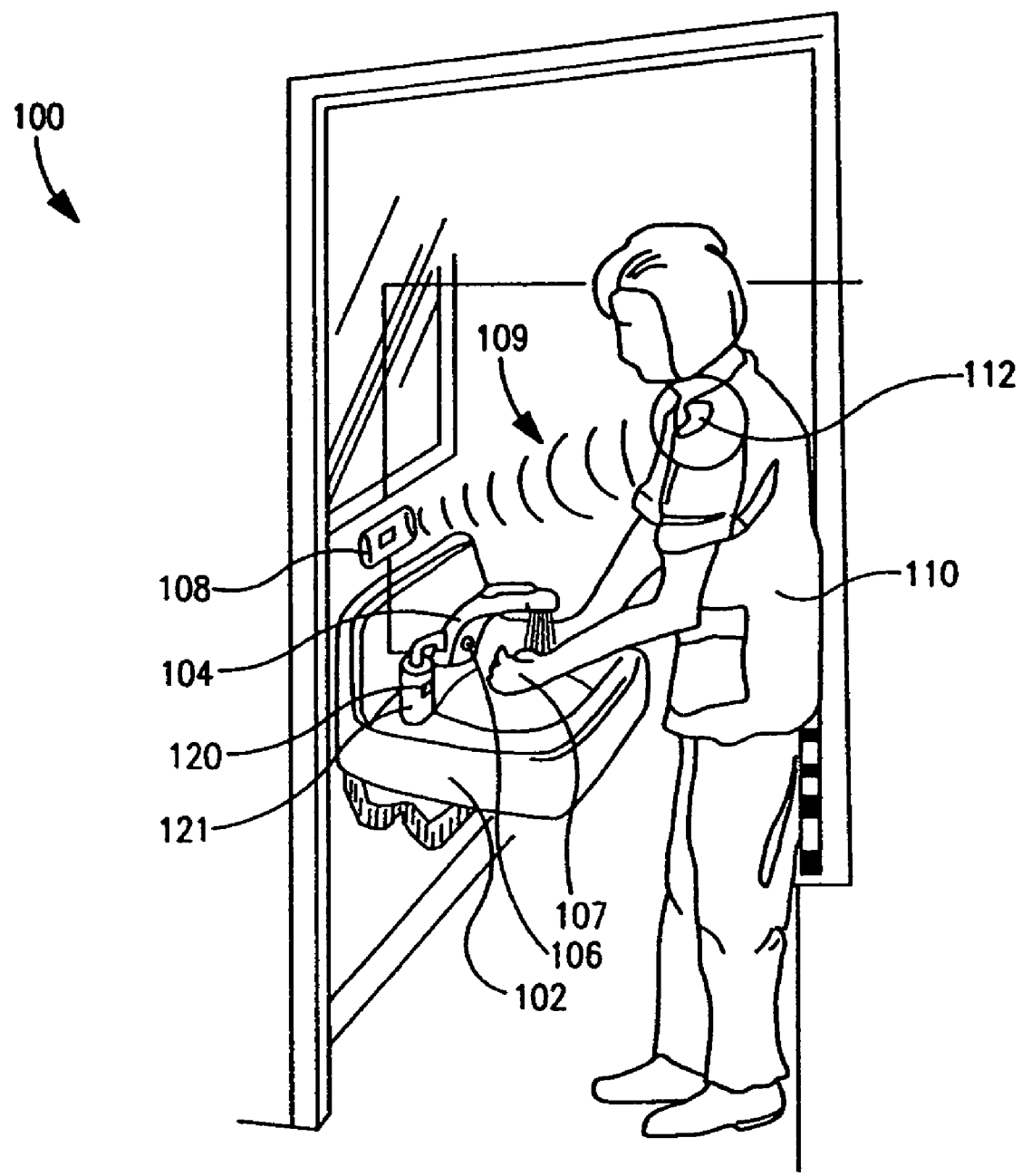
FIG. 2 shows a caregiver wearing a badge interacting with a handwashing device of the hygiene monitoring system.

The caregiver badges 112 are generally worn by persons to be monitored such as caregiver 110 shown in FIG. 2. The caregiver badges 112 are generally operable to communication identification information to the sensors 108, 118. Accordingly, the badges 112 and the sensors 108, 118 generally each include a receiver, a transmitter, a combination transmitter and receiver, a transceiver, or other receiving or transmitting mechanisms suitable for communicating identification information between the badges 112 and the sensors 108, 118.

For example, each badge 112 of the exemplary embodiment includes an infrared (IR) transmitter which transmits an identification signal 109, which may include, for example an identification code specific to the person wearing the badge 112. Further, each sensor 108, 118 of the exemplary embodiment includes a receiver operable to receive the identification signals 109 transmitted by badges 112. Further, each sensor 108, 118 is operable to forward the information received to the master station 129. In this manner, the location of each caregiver 110 wearing a badge 112 may be tracked as the caregiver 110 moves throughout the facility. Besides providing the master station 129 with identification information about the caregiver 110, functions (e.g. deactivating a nurse call light) may be triggered upon reception of the identification signal by a sensor 118 associated with the function (e.g. a sensor in the patient room associated with the nurse call light).

In an exemplary embodiment, each badge 112 includes an IR transmitter. The IR transmitter transmits the identification signal 109 to master station 129 via the sensors 108, 118. For example, as diagrammatically illustrated in FIG. 2, the IR transmitter of a badge 112 transmits the identification signal 109 to an IR receiver of a sensor 108 mounted above a handwashing device such as sink 102. The sensor 108 then provides the information received via the identification signal 109 to the master station 129 for further processing and recording.

Each badge 112 may further include an RF transmitter which also transmits the identification signal 109 to the master station 129. The advantage of transmitting using both the IR and RF transmitters is that if the IR transmitter becomes obscured the RF signal should still be detectable. The RF transmitter may also be used to transmit an alert signal in response to the pressing of a button on the badge 112.

Figure 5:
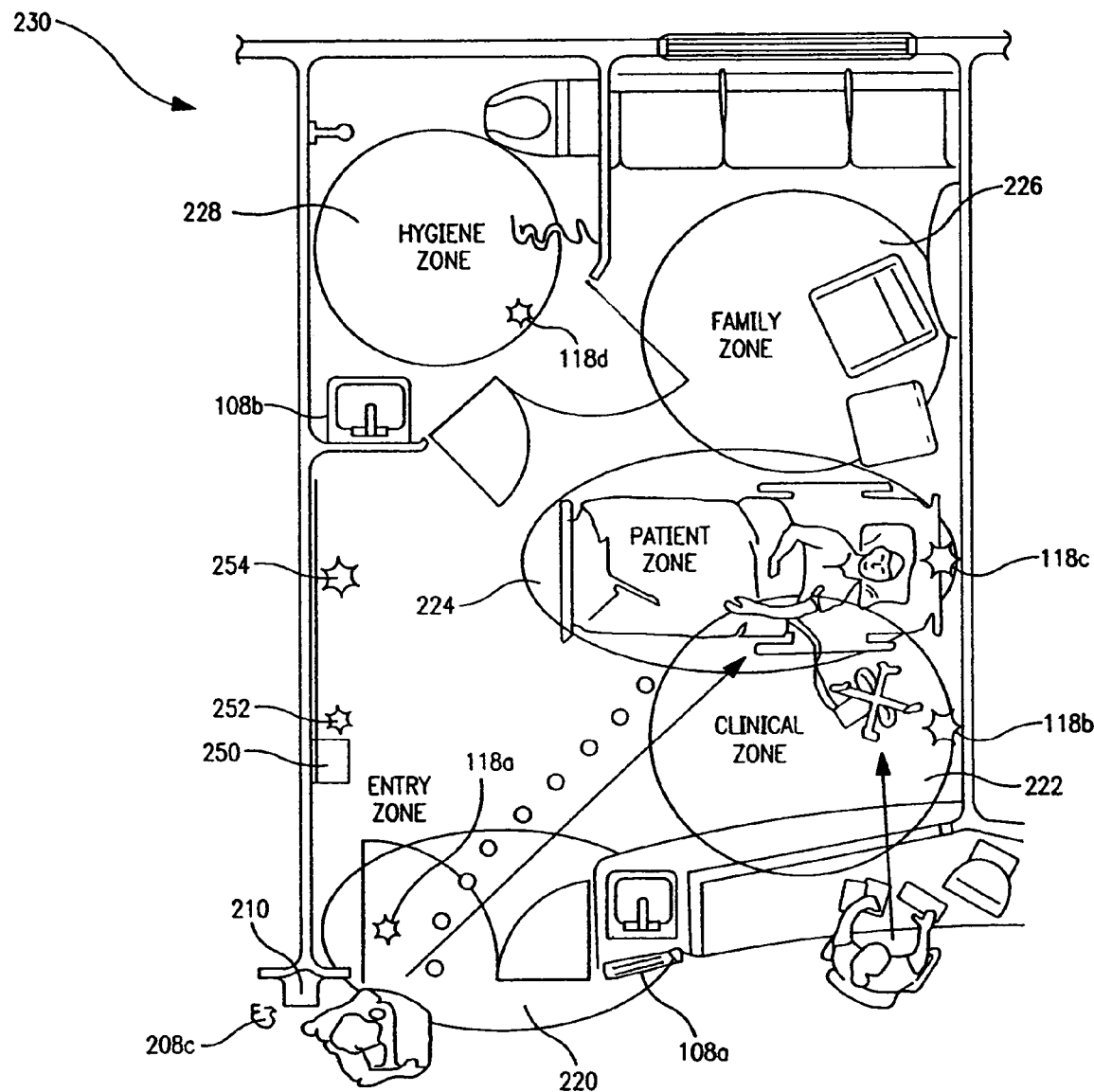
FIG. 5 shows a pictorial representation of a multi-zonal patient room.

Each badge 112 may further include an RF receiver that is operable to receive a signal, such as handwash signal 184 in FIG. 5, from the master station 129, wherein the signal includes the identification information for the badge 112 and status information about the caregiver 110 wearing the badge 112. The status information relates to the caregiver's compliance with the handwashing standards. Dependent upon the type of status received, the badge 112 is operable to activate either a visual, audible or tactile alert indicator 116.

In one embodiment of the hygiene monitoring system 100, visitors and patients are also provided with badges 112 so that their movements throughout the facility may be monitored. In such an embodiment, visitors and patients are given active badges which actively transmit an identification signal. In an alternative embodiment, visitors and patients are given passive badges which transmit an identification signal when polled by anyone of a plurality of transmitters located throughout the facility. The advantage of the passive badges are that they are relatively inexpensive and have a limited read range (approximately nine feet). The limited read range of the passive badges allows the location of the visitors and patients (or other objects) to be tracked more closely. By providing badges 112 to visitors the system is able to track the exposure each visitor and hence the patient's they come in contact with has had with other contamination zones. Additionally, providing badges 112 to the patients allows the system to track the exposure each patient has with other contamination zones within the facility as the patient moves about the facility.

The equipment badges 113 are generally attached to equipment 115 (e.g. IV pumps, ventilators, carts, diagnostic equipment, or the like) to be monitored by the hygiene monitoring system 100 and generally enable the location of equipment 115 to be tracked throughout the facility. The equipment badges 113 are generally operable to communicate identification information to the sensors 118. Accordingly, the badges 113 and the sensors 118 generally each include a receiver, a transmitter, a combination transmitter and receiver, a transceiver, or other receiving or transmitting mechanisms suitable for communicating identification information between the badges 113 and the sensors 118. As a result of providing the hygiene monitoring system 100 with information concerning the location of equipment 115, the hygiene monitoring system 100 may further base determinations of hygiene compliance based upon the location of the equipment 115 and/or persons' interactions with such equipment 115.

The usage sensors 119 are generally associated with equipment 115 in the facility and generally enable the hygiene monitoring system 100 to monitor the use of such equipment 115. For example, the usage sensors 119 may be attached to the electrical plug of the equipment 115 to determine whether the equipment 115 is drawing a current. Further, the usage sensors 119 may be included in the equipment badge 113 or be separate from the equipment badge 113 attached to the equipment 115. The usage sensors 119 enable the hygiene monitoring system 100 to base determinations of hygiene compliance upon actual use of equipment 115. Furthermore, by reporting when the equipment 115 is activated and de-activated, the usage sensors 119 enable the hospital to charge patients for the actual amount of time the equipment 115 was used instead of utilizing national averages based on the type of illness of the patient.

Likewise, the cleaning sensors 121 are generally associated with equipment 115 in the facility and generally enable the hygiene monitoring system 100 to monitor cleaning of such equipment 115 by providing the hygiene monitoring system 100 with information associated with the cleaning of the equipment 115. For example, the cleaning sensors 121 may be implemented as a switch or button which when activated provides the master station 129 with information indicating that there as been an attempt to clean the equipment 115. Alternatively, the cleaning sensors 121 may be implemented to detect moisture and/or physical contact associated with the cleaning process. In an exemplary embodiment, the master station 129 and/or the cleaning sensor 121 further ensures that adequate cleaning of the equipment 115 has been performed by requiring that the person cleaning the equipment 115 be in the proximity of the equipment 115 for a minimum amount of time and/or moisture associated with the cleaning process be detected for the minimum amount of time and/or physical contact associated with the cleaning process be detected for the minimum amount of time.

The equipment badges 113 may be implemented in the same manner as the caregiver badges 112. Alternatively, the equipment badges 113 may be implemented with general active badges which actively transmit a signal including the state of the associated usage sensor 119, the state of the associated cleaning sensor 121 and identification information associated with the equipment 115. As yet another alternative, the equipment badges 113 may be implemented as passive badges which transmit a signal including the state of the associated usage sensor 119, the state of the associated cleaning sensor 121 and the identification information for the equipment 115 when polled by the hygiene monitoring system 100. To support the passive badge embodiment, the hygiene monitoring system 100 may include transmitters in the patient room to poll the passive badges. The transmitters, in one embodiment, further include an associated sensor to detect the signals transmitted by the badges.

The badges 112, 113 and sensor 108, 118 may further utilize anti-collision technology which allows for information to be transferred between a single sensor 108, 118 and multiple badges 112, 113 in a simultaneous or pseudo-simultaneous (e.g. TDMA, CDMA) manner. Any commercially available anti-collision technology may be used. Use of this technology allows for several badges 112, 113 to be detected at the same time by the same sensor 108, 118 thereby providing the hygiene monitoring system 100 with the ability to identify caregivers and equipment 115 in close proximity to one another and accurately track their respective hygiene status. Thus, when a team of doctors and nurses is caring for a patient, the hygiene monitoring system 100 is able to identify the individual persons within the group of caregivers and monitor their hygiene status. Likewise, the hygiene monitoring system 100 is operable to determine individual persons of a group of persons in front of a particular handwashing device 101 during a handwashing.

Additional details concerning the structure and function of a suitable system for locating and tracking persons and which may be utilized to support various other features of the present invention are disclosed in U.S. Pat. No. 5,561,412, the disclosure of which is hereby incorporated by reference. Another location and tracking system is disclosed in U.S. Pat. No. 6,344,794 which is hereby incorporated by reference. Additional location and tracking systems are disclosed in U.S. Pat. Nos. 4,275,385; 4,601,064; Re 35,035; 5,633,742; 5,745,272; 5,818,617; 5,119,104; 5,387,993; 5,548,637; 5,572,195; 5,291,399; 5,455,851; 5,465,082; 5,515,426; 5,594,786; 5,689,229; 5,822,418; 5,822,544; 5,699,038 and 5,838,223.

Shown in FIG. 2 is an exemplary sink 102 which may be used to implement the handwashing devices 101 of the present invention. As shown in FIG. 2, the exemplary sink 102 includes a "hand free" faucet 104 having an IR sensor and an faucet monitoring device 106. However, it is within the scope of the present invention to include a faucet 104 which is not "hands free" and a separate IR sensor or an IR sensor that is activated upon activation of the faucet 104. Water is dispensed from faucet 104 when the presence of the caregiver's hands 107 are detected by faucet monitoring device 106 or when the caregiver otherwise activates faucet 104. The IR sensor of the "hands free" faucet 104 senses the heat (IR energy) radiated from caregiver hands 107. The sensed heat is an indication to faucet monitoring device 106 that hands 107 are positioned below the faucet and are ready to be wetted. Upon activation of faucet 104 a washing compliance signal is generated and forwarded to master station 129 by faucet monitoring device 106.

Alternatively, the faucet monitoring device 106 may include a photosensor or other type of non-contact sensor. Additionally, a sensor may be mounted within faucet 104 to determine when water is expelled from faucet 104. Yet another alternative faucet monitoring device 106 includes a sensor 120 on a soap dispenser 121 to monitor the usage of soap during the handwashing. Faucet monitoring device 106 could include multiple sensors such as an IR sensor to sense the presence of hands 107 and a soap dispenser sensor 120 to detect the usage of soap during washing.

The compliance signal generated by faucet monitoring device 106 and the identification signal received by sensor 108 combine to provide information about the identity of caregiver 110 in front of sink 102 and whether or not caregiver 110 washed his/her hands 107. Both signals are generated and recorded without any input required from caregiver 110. In the exemplary embodiment, the compliance signal is generated over eleven input lines which connect faucet monitoring device 106 with sensor 108, one line for each bit. The first eight bits communicate data from the faucet monitoring device 106 to sensor 108 while the last three bits communicate data from sensor 108 to faucet monitoring device 106. Bit 1 is used as a fault bit. A "0" value indicates that the faucet is operating properly while a "1" value indicates that the faucet is not operating properly. Bits 2 and 3 are handwashing status bits. The combination of bits 2 and 3 have the following states: "00" no handwashing procedure in progress, "10" handwashing procedure in progress, "11" successful handwashing procedure, and "01" failed handwashing procedure. Bits 4–8 provide an indication as to the maintenance status of the various components related to faucet monitoring device 106, such as faucet 104 and soap dispenser 121. A "1" value for bit 4 indicates that the soap container is low, a "1" value for bit 5 indicates that the soap caseate needs to be changed, a "1" value for bit 6 indicates that the soap path needs to be changed, and a "1" value for bit 7 indicates that the towel container is low. It is within the scope the invention to monitor various other parameters in place of or in addition to the ones listed above.

Bits 9–11 are used as input to faucet monitoring device 106 from sensor 108. Bit 9 is used as a badge presence indicator. In one embodiment, bit 9 provides a "1" value when a identification signal 109 is detected by sensor 108. In another embodiment, bit 9 provides a "0" value when sensor 108 is receiving an identification signal 109 from a contaminated caregiver 110 and a "1" value when sensor 108 is receiving an identification signal 109 from a non-contaminated caregiver 110 or no identification signal is being received. Bit 10 is used to communicate whether sensor 108 is functioning properly and if sensor 108 is able to communicate with master station 129. Bit 11 is used to send a message to faucet monitoring device 106 to start a self test procedure. In one embodiment, faucet monitoring device begins monitoring for compliance only when the presence of hands 107 are detected and bit 9 from sensor 108 indicates that a identification signal has been detected.

When a caregiver 110 is positioned in front of sink 102, sensor 108 detects identification signal 109 transmitted by badge 112 as shown diagrammatically in FIG. 2. Sensor 108 is mounted above sink 102 and includes an IR receiver connected to the hygiene monitoring system 100. The received identification signal is forwarded onto master station 129 and recorded. It is within the scope of the present invention as presently perceived to use a RF, ultrasonic or other suitable system for detecting the presence of a caregiver in contamination zones, patient rooms, or by sink 102. Alternative devices can be used for sensor 108 such as a radio receiver if badge 112 transmitted a radio signal instead of an infrared signal.

Sensor 108 combines the compliance signal from faucet monitoring device 106, bits 1–8, and the received identification signal 109. The combined signal or packet is transmitted to or made available to or detected by master station 129. In a preferred embodiment, sensor 108 includes a radio frequency transmitter to transmit a radio frequency transmission to master station 129. In one embodiment the combined signal or packet consists of 35 bits. Bits 1 and 2 are start bits. Bits 3–10 are a portion of identification signal 109, the LO Byte of the caregiver ID. Bit 11 is a parity bit for use as an error check for bits 3–10. Bits 12–19 are a portion of identification signal 109, the HI Byte of the caregiver ID. Bit 20 is a parity bit for use as an error check of bits 12–19. Bits 21–28 are the eight bits sent to sensor 108 from faucet monitoring device 106. Bit 29 is a parity bit for use as an error check for bits 21–28. Bits 30–33 are extra bits for expansion use, such as to communicate the status of various pieces of equipment, lights, IV pumps, etc. Bit 34 is a parity bit for use as an error check for bits 30–33. Bit 35 is a stop bit.

Besides sinks 102, the handwashing devices 101 as depicted in FIG. 5 may also be implemented with automatic alcohol dispenser 210, dispensers 250, or other monitored devices with which a person may successfully wash her hands in accord with a hygiene policy. In some environments, it is permissible for caregiver 110 to cleanse hands 107 with an alcohol towelette dispensed by alcohol dispenser 210, as opposed to washing her hands in front of a sink with soap and water. Therefore, in one embodiment of the hygiene monitoring system 100, the hygiene monitoring system 100 further tracks whether persons wash their hands with an alcohol towelette that is dispensed from the automated alcohol dispenser 210 and updates compliancy information based upon such determinations. To this end, the hygiene monitoring system 100 utilizes a sensor such as sensor 108C proximate with the alcohol dispenser 210 to determine whether the person has washed her hands via the alcohol dispenser 210.

In some environments, it is also permissible for caregiver 110 to cleanse hands 107 with a waterless hand sanitizer such as an alcohol based gel dispensed from dispenser 250. An exemplary dispenser 250 is the "Bag-in-a-Box Dispenser" which receives a bladder filled with hand sanitizer. Dispenser 250 further includes a sensor 108 to detect identification signal 109 transmitted by badge 112. Sensor 108 either detects signal 109 and then waits to sense a dispensing of hand sanitizer or is activated upon the detection of hand sanitizer being dispensed from dispenser 250. Therefore, in one embodiment of the hygiene monitoring system 100, the hygiene monitoring system 100 further tracks whether persons wash their hands with hand sanitizer dispensed from dispenser 250 and updates compliancy information based upon such determinations.

In a further embodiment, the dispenser 250 is implemented as a portable dispenser, similar to a pump bottle or squeeze bottle, which is carried by caregiver 110. Portable dispenser 250 includes a sensor to detect when sanitizer is dispensed from dispenser 250. An example sensor would be a sensor to detect the movement of the stem of a hand pump on a pump bottle or the movement of sanitizer through an orifice. The use of portable dispenser 250, which is small enough to fit in the caregiver's coat or pocket, provides caregiver 110 with easy access to hand sanitizer and does not require additional hardware such as sensors and dispensers to be mounted on the wall in various locations throughout the hospital.

Portable dispenser 250 either includes a transmitter such as equipment badge 113 or a combination transmitter and receiver. In one embodiment wherein only a transmitter is used, portable dispenser 250 is assigned to caregiver 110 such that the equipment badge 113 of the dispenser 250 either transmits an identification signal which is identical to or incorporates a portion of caregiver identification signal 109 or an identification signal which is associated with caregiver 110 in a database at master station 129. In another embodiment wherein both a transmitter and a receiver or a transceiver is associated with portable dispenser 250, portable dispenser 250 receives identification signal 109 from caregiver badge 112. Portable dispenser 250 then forwards a signal such as the caregiver identification signal plus a compliance signal onto master station 129 either directly or through sensor 118.

Alert indicators 116 generally provide caregivers with feedback concerning their current contamination status and/or infraction status. In one embodiment, visual alert indicators 116 are included in the proximity of sinks 102, such as on faucet 104. The visual alert indicators 116 are capable of providing textual messages either continuously or at defined intervals and potentially other visual cues such as blinking diodes. The visual alert indicators 116 may provide feedback to caregiver 110 on whether a successful handwashing has been accomplished or not. The visual alert indicators 116 may also provide messages such as "HANDWASHING CONFIRMED" or "SUCCESSFUL" for a properly completed handwashing event. The visual alert indicators 116 may also provide messages such as "WARNING HANDWASHING FAILED" or "FAILED" when caregiver 110 has not completed a successful handwashing. An unsuccessful handwashing would occur for example when caregiver 110 uses water but not soap. Further, the visual alert indicators 116 also provides information about the maintenance state of the faucet, sink or other devices. Example messages include "SINK READY FOR USE", "SELF-TEST IN PROGRESS", "WARNING! SOAP CONTAINER LOW", "WARNING! CHANGE SOAP CASSETTE", "WARNING! CHANGE SOAP PATH", or "WARNING! TOWEL CONTAINER LOW."

Figure 3:
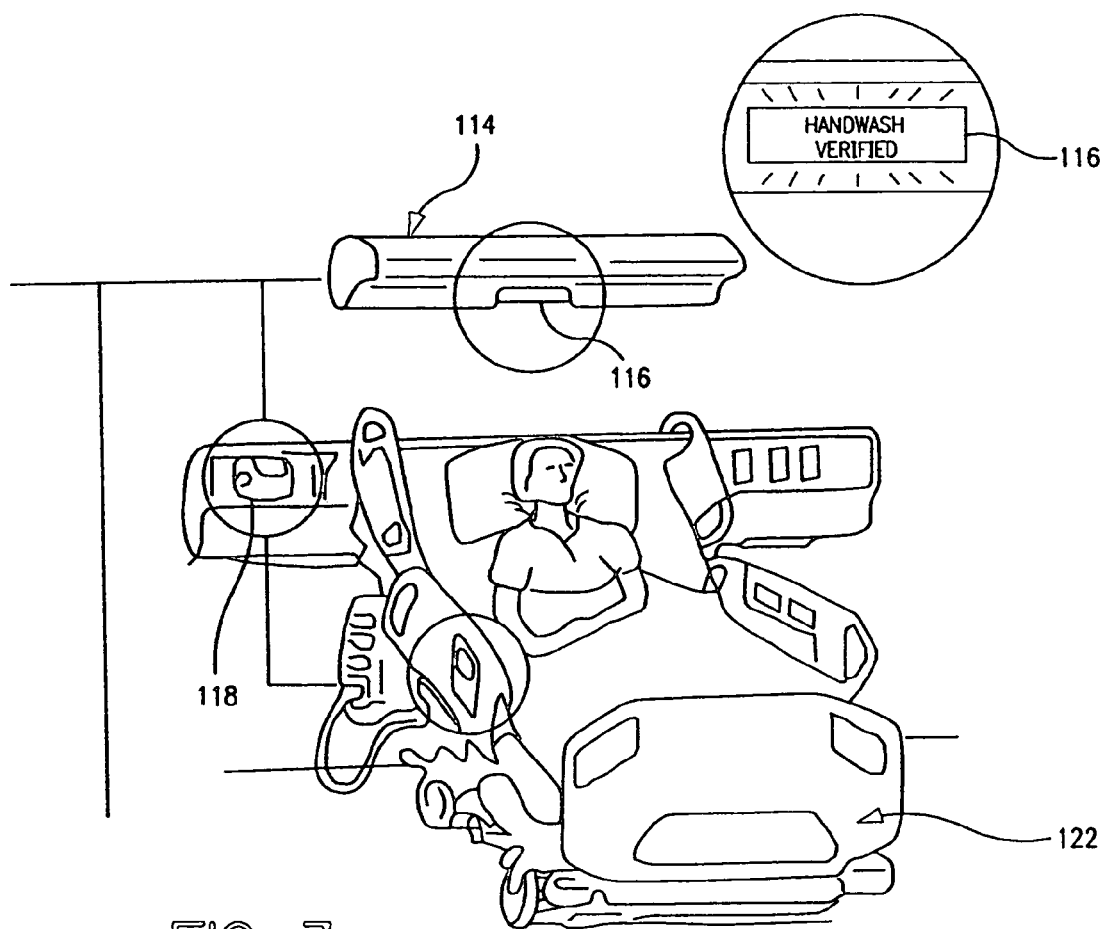
FIG. 3 shows a patient room and exemplary alarm units of the exemplary hygiene monitoring system.
Figure 4:
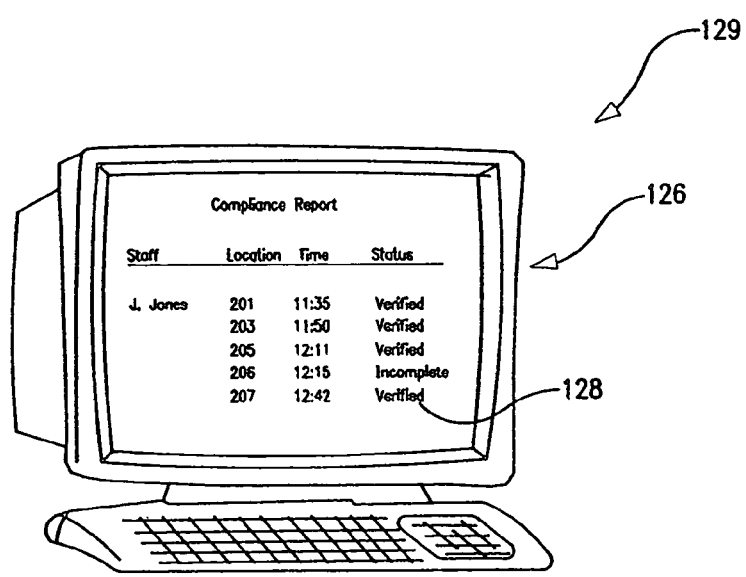
FIG. 4 shows an exemplary hygiene compliance report being displayed by an exemplary master station of the exemplary hygiene monitoring system.

The alert indicators 116 may also be placed in various locations in the patient rooms such as on bed 122, on the wall of the patient's room, or incorporated into an overhead lighting fixture 114 as shown in FIG. 3. Such alert indicators 116 may be implemented to either remind caregiver 110 to wash hands 107 or to indicate that a handwashing compliance signal has been recorded. The timing for each type of indication is explained below in more detail with reference to FIG. 6 and FIG. 8. For example, such an alert indicator 116 may include a set number of lights or a single light which are covered by a colored semi-transparent shield. Various indications are given based on which lights in the set of lights are turned on and which lights in the set of lights are turned off or whether any of the lights in the set of lights are flashing. In one embodiment, the light shield contains a graphic message such as "handwash verified" as shown in FIG. 3.

In embodiments where alert indicators 116 are located throughout a facility, the master station 129 may cause a signal to be directed to an alert indicator that is in close proximity to the caregiver 110. For example, the master station 129 may provide a handwash signal to an alert indicator 116 in the same room as the caregiver 110 when a handwash condition exists for the caregiver 110. In such an embodiment, the alert indicators 116 may be either "wirelessly connected" or "hard-wired" to the master station 129. Moreover, the alert indicator 116 in such embodiments could be implemented as a bank of lights including a light corresponding to each person monitored, or it may be implemented with remote units such as, for example, banks of lights or speakers that have been mounted in various locations in the facility.

Alert indicators 116 may also be implemented in a portable manner. For example, alert indicators 116 may be incorporated into badges 112 or carried by caregiver 110 as a separate unit, such as a pager-type unit. Such alert indicators 116 would include a sensor to receive handwash signal 184 provided by the hygiene monitoring system 100. In one embodiment, the portable alert indicators 116 include a radio frequency receiver to receive a signal from master station 129, sensor 108 or other sensors such as sensor 118. The received signal includes the caregiver ID to distinguish between different caregivers 110 and an infraction level code to communicate the status of the caregiver 110, either in compliance with the handwashing standards or out of compliance with the handwashing standards.

The alert indicators 116 may be implemented to vary output based upon the number of non-compliance data 140 which is recorded by system 100 for caregiver 110. In one embodiment, lights are included on badge 112, such as light emitting diodes. When caregiver 110 is complying with handwashing regulations the lights on badge 112 are off. When caregiver 110 enters a contamination zone the lights or at least one of the lights blinks yellow to indicate that caregiver 110 has entered a contamination zone. If caregiver 110 violates the handwashing standards, i.e. a non-compliance signal 140 is generated, the lights or at least one of the lights slowly blinks red. If caregiver 110 does not wash hands 107 at this point and violates the handwashing standards a second time the lights or at least one of the lights blinks red at a faster rate. If caregiver 110 commits a third consecutive infraction of the handwashing standards then the lights or at least one of the lights blinks red very fast. If the caregiver 110 commits a fourth consecutive infraction of the handwashing standards then the lights or at least one of the lights remains on and an alarm is sounded by an audible or tactile indicator on badge 112.

It is within the scope of the invention as presently perceived to implement alert indicators 116 to include visual, audible and/or tactile indicators which respectively produce visual signals, audible signals, and tactile signals. An example of an visual indicator is a LED, an example of an audible indicator is a speaker, and an example of a tactile indicator is a vibration device similar to a pager vibration device.

Multi-Zonal Patient Rooms

In FIG. 5 is shown an example of patient room 230 having generally five different zones. An entry zone 220, a clinical zone 222, a patient zone 224, a family zone 226 and a hygiene zone 228. All of these zones except for the family zone 226 has a sensor 118 associated therewith. As shown in FIG. 5, caregiver 110 enters patient room 230 through the entry zone 220. As the caregiver enters the entry zone 220, the identification signal 109 broadcasted by caregiver badge 112 is detected by sensor 118A. If caregiver 110 proceeds to the patient zone 224, then the signal broadcasted by the caregiver badge 112 is detected by sensor 118C. Patient zone 224 is a critical contamination zone. Therefore, the hygiene monitoring system 100 initiates the first handwashing monitoring logic depicted in FIG. 6. Also shown in FIG. 5 are various handwashing devices 101 such as two sinks 102A and 102B each containing a sensor 108A and 108B, respectively, an automated alcohol dispenser 210, and a dispenser 250 of hand sanitizer.

In one embodiment, patient room 230 further includes a sensor 254. Unlike sensors 118A–118D which generally receive signals 109 when caregiver 112 is within the corresponding zone 220, 222, 224 and 228, sensor 254 generally receives signal 109 when caregiver 112 is present in patient room 230 independent of whether caregiver 112 is within one of the zones 220, 222, 224 and 228 or elsewhere in patient room 230. As such, sensor 254 is a low resolution aspect of the hygiene monitoring system 100 while sensors 118A–118D are a high resolution aspect of the hygiene monitoring system 100. Sensor 254 is designed to be compatible with badge 112. Therefore, if badge 112 emits only an IR signal 109 then sensor 254 should be designed to receive an IR signal 109. Alternatively, if badge 112 emits both an IR signal 109 and a RF signal 109 then sensor 254 should be designed to receive either IR signal 109, RF signal 109 or a combination of IR signal 109 and RF signal 109.

First Handwashing Logic

Figure 6:
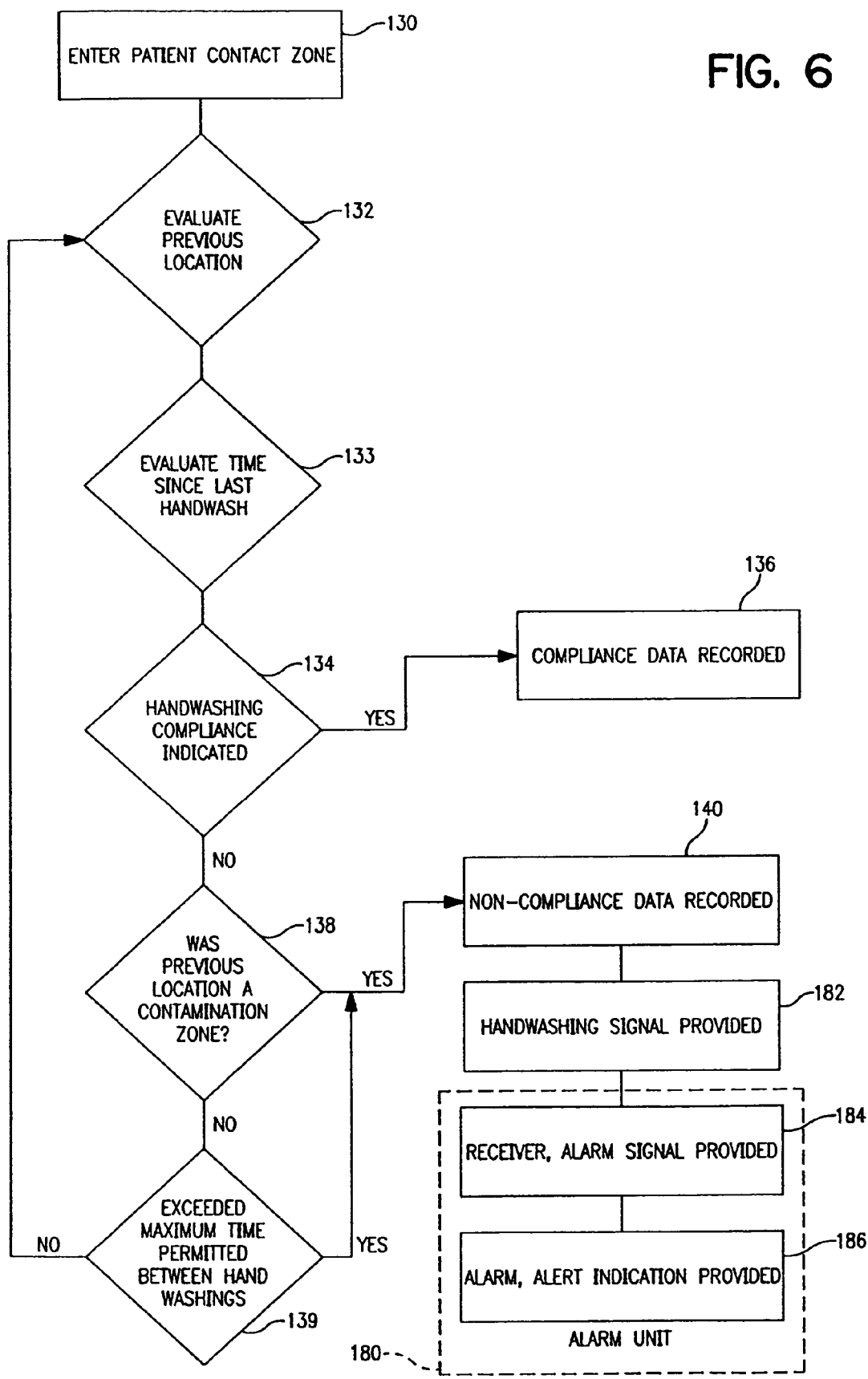
FIG. 6 shows a flowchart representation of first handwashing logic used by the hygiene monitoring system.

A flowchart is depict in FIG. 6 which illustrates first handwashing logic implemented by the hygiene monitoring system 100. In the exemplary embodiment, the master station 129 includes software which when executed by the master station 129 causes the hygiene monitoring system 100 to implement the first exemplary handwashing logic as depicted in FIG. 6. However, while the exemplary embodiment of the hygiene monitoring system 100 implements the handwashing logic of FIG. 6 with software executed by the master station 129, the handwashing logic of FIG. 6 may alternatively be implemented with hardware incorporated in a central device such as the master station 129 or distributed amongst the other components of the hygiene monitoring system 100. Furthermore, the software can be implemented as a stand alone program or can be integrated into the software of an existing system for locating and tracking persons in a facility.

In an exemplary embodiment, the hygiene monitoring system 100 invokes execution of the first handwashing logic as represented by block 130 every time a caregiver identification signal 109 is detected in a nurse or patient contact zone, such as a patient room or nurse station. The presence of caregiver 110 in such a zone is determined by the hygiene monitoring system 100 upon the detection of identification signal 109. The hygiene monitoring system 100 determines, based on the previous recorded locations of caregiver 110, if caregiver 110 has complied with handwashing standards. Therefore, the hygiene monitoring system 100 monitors for compliance based upon the occurrences of specific events. The hygiene monitoring system 100 also evaluates the time elapsed between handwashings to determine if a preset maximum time has been exceeded. Therefore, the hygiene monitoring system 100 further monitors for compliance based upon frequency of handwashings.

Once execution of the first handwashing logic is initiated, the hygiene monitoring system 100 evaluates the previous location of caregiver 110 as indicated by block 132. The current and previous locations of caregiver 110 are determined and stored by the hygiene monitoring system 100 during the cause of operation. The elapsed time since the last recorded compliance data record is determined by the hygiene monitoring system 100, as indicated by block 133. The hygiene monitoring system 100 next determines, as indicated by block 134, if a handwashing compliance signal has been received in conjunction with the previous location of caregiver 110. A handwashing compliance signal is generated by faucet monitoring device 106 or other handwashing device when caregiver 110 washes hands 107 and is transmitted to or detected by master station 129. If a handwashing compliance signal has been received, the compliance data is recorded, as indicated by block 136. If a handwashing compliance signal was not recorded, the hygiene monitoring system 100 moves to block 138 which determines whether the previous location of caregiver 110 was a contamination zone.

A contamination zone is any area designated by the hospital where after caregivers have entered they must wash her hands. Typically, a contamination zone is an area in which caregiver 110 is susceptible to contact with infectious agents. Examples are a patient room, a bath room, a waste station or a nurse station. If the previous location of caregiver 110 was a designated contamination zone a handwashing non-compliance data is recorded as indicated by block 140. The non-compliance data is recorded because caregiver 110 has left a contamination zone and entered a nurse or patient contact zone without washing hands 107, thereby putting patients and colleagues at risk of infection.

If the previous location of caregiver 110 was not a contamination zone at block 138, the hygiene monitoring system 100 continues to block 139 and determines if the maximum time permitted between handwashings has been exceeded. If the maximum time has been exceeded, then a handwashing non-compliance record is recorded by block 140. If the previous location of caregiver 110 was not a contamination zone and the maximum time permitted between handwashings has not been exceeded, the hygiene monitoring system 100 returns to block 132 and evaluates the twice previous location of caregiver 110. If a handwashing compliance was not indicated for the twice previous location nor was the twice previous location a contamination zone, the hygiene monitoring system 100 returns to block 132 and evaluates the thrice previous location of caregiver 110, assuming that the maximum time permitted between handwashings has not been exceeded. The hygiene monitoring system 100 continues until either a handwashing compliance record is recorded by block 136 or a handwashing non-compliance record is recorded by block 140.

If a non-compliance data record is recorded by block 140, the hygiene monitoring system 100 generates a handwash alarm signal as represented by block 182. The hygiene monitoring system 100 then sends the handwash alarm signal to an alert indicator 116 of caregiver 110. The sensor on the alert indicator 116 receives the alarm signal represented by block 184, and the alert indicator 116 provides the caregiver 110 with an alert signal, represented by block 186. Example alert signals include visual signals, audible signals, tactile signals or combinations thereof.

Figure 7:
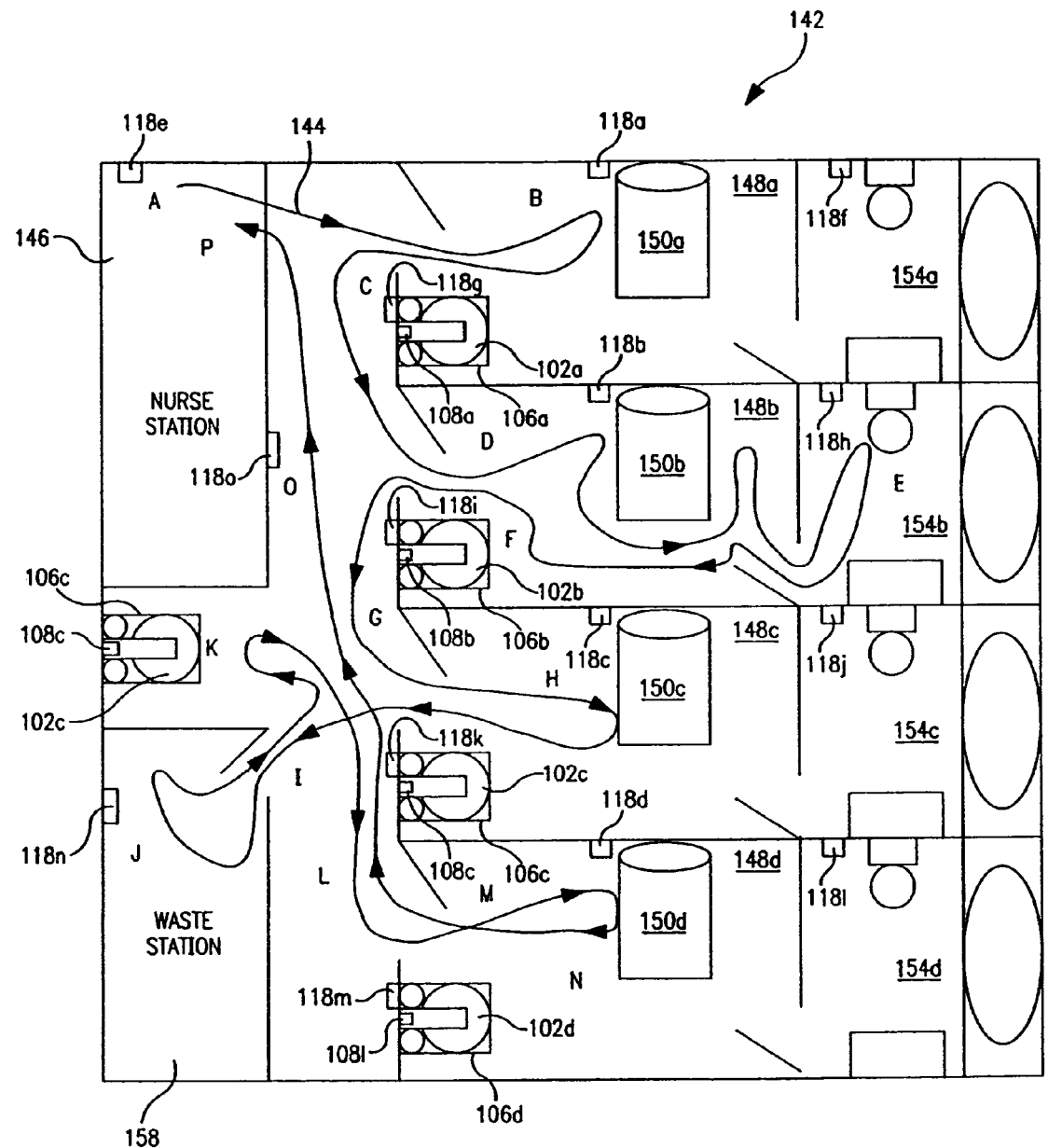
FIG. 7 shows an exemplary path that a caregiver may take through a facility over a period of time.

Referring now to FIG. 7, there is depicted a hospital ward 142 and a sample path 144 taken by caregiver 110 through the hospital ward 142. The location of caregiver 110 is detected by sensor 118a–118d when caregiver 110 is next to patient bed 150a–150d, respectively. The location of caregiver 110 is detected by sensor 108a–108e when caregiver 110 is near sinks 102a–102e, respectively. At other locations in hospital ward 142, the location of caregiver 110 is detected by sensors 118e–118o.

Caregiver 110 starts at nurse station 146 as indicated by position (A). Caregiver 110 next leaves nurse station 146 and enters a patient room 148a and approaches the patient bed 150a, as indicated by position (B). Caregiver's badge transmits a signal which is detected by sensor 118a and read by master station 129 indicating that the caregiver is by position (B), thereby initiating the hygiene monitoring system 100 to begin execution of the handwashing monitoring logic because caregiver 110 has entered a nurse or patient contact zone, near patient bed 150a. The previous position (A) of caregiver 110 does not have a handwashing compliance signal recorded and position (A) is a contamination zone. Therefore, a non-compliance data record is recorded at block 140.

Caregiver 110 next leaves position (B) without washing hands 107 at sink 102a and enters a second nurse or patient contact zone, patient room 148b next to patient bed 150b, as indicated by position (D). Once again, the hygiene monitoring system 100 initiates execution of the first handwashing logic because caregiver 110 has entered a nurse or patient contact zone, near patient bed 150b. The previous position (C) of caregiver 110 does not have a handwashing compliance signal recorded. However, position (C), a hallway, is not a contamination zone. After determining that the maximum time permitted between handwashings has not been exceeded, the twice previous caregiver location, position (B) in patient room 148a near bed 150a is evaluated. Position (B) does not have a handwashing compliance signal recorded. However position (B) is a contamination zone. Therefore, a non-compliance data record is recorded at block 140.

Caregiver 110 next enters bathroom 154b, at position (E) and then washes hands 107 at sink 102b, position (F). Therefore, a handwashing compliance signal is generated by faucet monitoring device 106b.

Caregiver 110 next enters a third nurse or patient contact zone at position (H), patient room 148c. Once again, the hygiene monitoring system 100 initiates execution of the first handwashing logic because caregiver 110 has entered a nurse or patient contact zone. The previous position (G) of caregiver 110 does not have a handwashing compliance signal recorded. However, position (G), a hallway, is not a contamination zone. After determining that the maximum time permitted between handwashings has not been exceeded, the twice previous caregiver location, position (F) in patient room 148b near sink 102b is therefore evaluated. Position (F) does have a handwashing compliance signal recorded. Therefore, a compliance data record is recorded at block 136.

Caregiver 110 continues on to position (J), a waste station 158, which is a contamination zone. Next, caregiver 110 washes hands at position (K), sink 102e. Therefore, a handwashing compliance signal is generated by faucet monitoring device 106e. The fact that caregiver 110 did not wash hands 107 between locations (H) and (J) is acceptable, as long as the maximum time permitted between handwashings has not been exceeded, because caregiver 110 did not enter a nurse or patient contact zone between locations (H) and (J).

Caregiver 110 continues on to position (M) a fourth nurse or patient contact zone, patient room 148d next to patient bed 150d. Once again, the software is initiated by central processing unit 126 and begins its handwashing monitoring logic. The previous position (L) of caregiver 110 does not have a handwashing compliance signal recorded. However, position (L), the hallway, is not a contamination zone. After determining that the maximum time permitted between handwashings has not been exceeded, the twice previous caregiver location, position (K) near sink 102e is evaluated. Position (K) does have a handwashing compliance signal recorded. Therefore, a compliance data record is recorded at block 136.

Caregiver 110 continues on to nurse station 146, position (P). Since caregiver 110 is in a nurse contact zone at position (P), the hygiene monitoring system 100 initiates execution of the first handwashing logic. The previous position (O) of caregiver 110 does not have a handwashing compliance signal recorded. However, position (O), a hallway, is not a contamination zone. After determining that the maximum time permitted between handwashings has not been exceeded, the twice previous caregiver location, position (N) in patient room 148d near bed 150d is evaluated. Position (N) does not have a handwashing compliance signal recorded. However position (N) is a contamination zone. Therefore, a non-compliance data record is recorded at block 140.

Caregiver 110 achieved a forty percent compliance rating, washed hands 107 two out of five required times, for path 144, as shown in FIG. 7. Compliance report 128 provides the compliance rating of caregiver 110 and provide information such as the time each compliance record was recorded, the time each non-compliance record was recorded, and the locations of each, see FIG. 13B.

The above handwashing monitoring logic may further utilize a delay timer to prevent a brief encounter with a patient contact zone to require a caregiver to wash her hands. For example, upon detecting the identification signal 109 from caregiver badge 112 within a patient zone, the hygiene monitoring system 100 will delay a preset amount of time before starting the handwashing monitoring logic, such as 15 seconds. If the identification signal 109 is still detected in the patient contact zone after the present amount of time has expired, then the handwashing monitoring logic begins. Therefore, a caregiver simply dropping off a lunch tray will probably not invoke the handwashing monitoring logic, while a caregiver who is interacting with a patient probably will invoke the handwashing monitoring logic.

Second Handwashing Logic

Figure 8A:
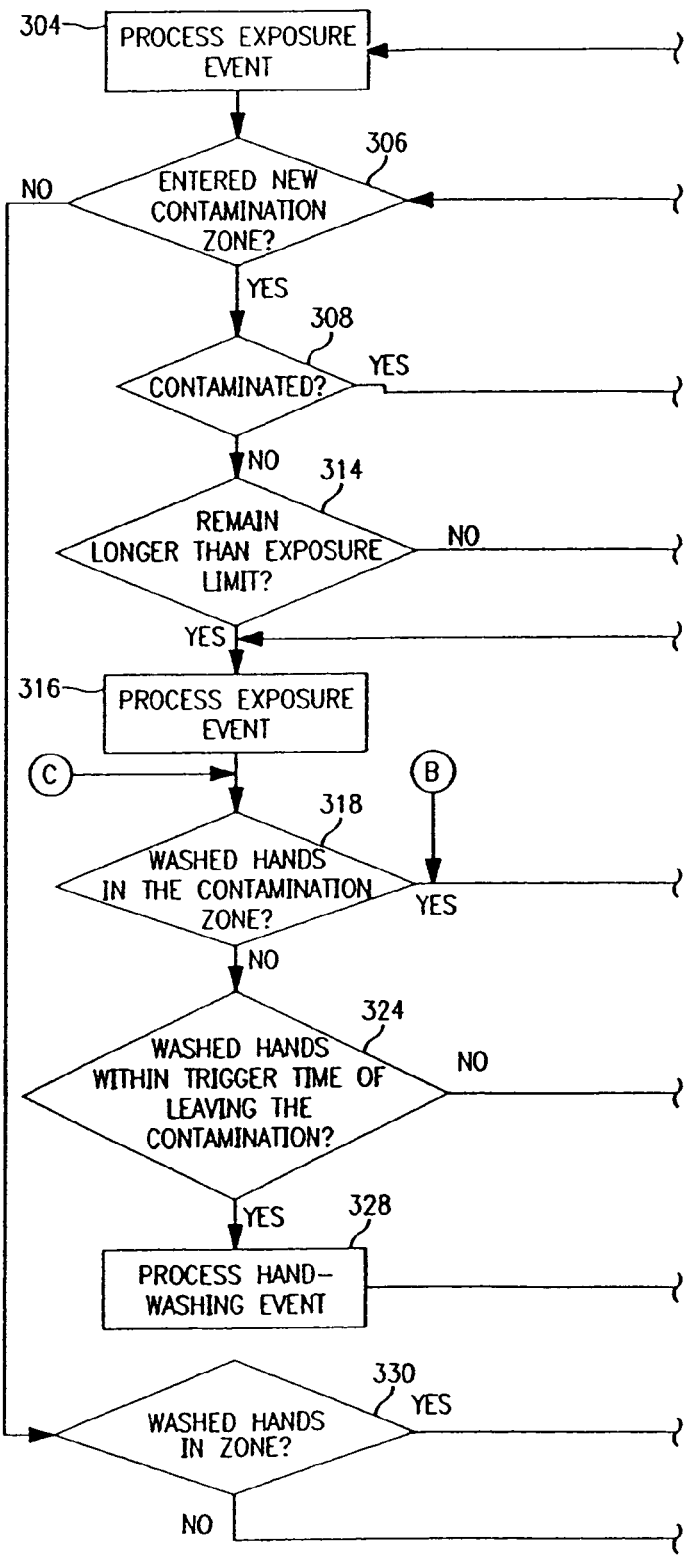
FIG. 8 is presented as FIG. 8a and FIG. 8b that together show a flowchart representation of second handwashing logic which may be used by the hygiene monitoring system.
Figure 8B:
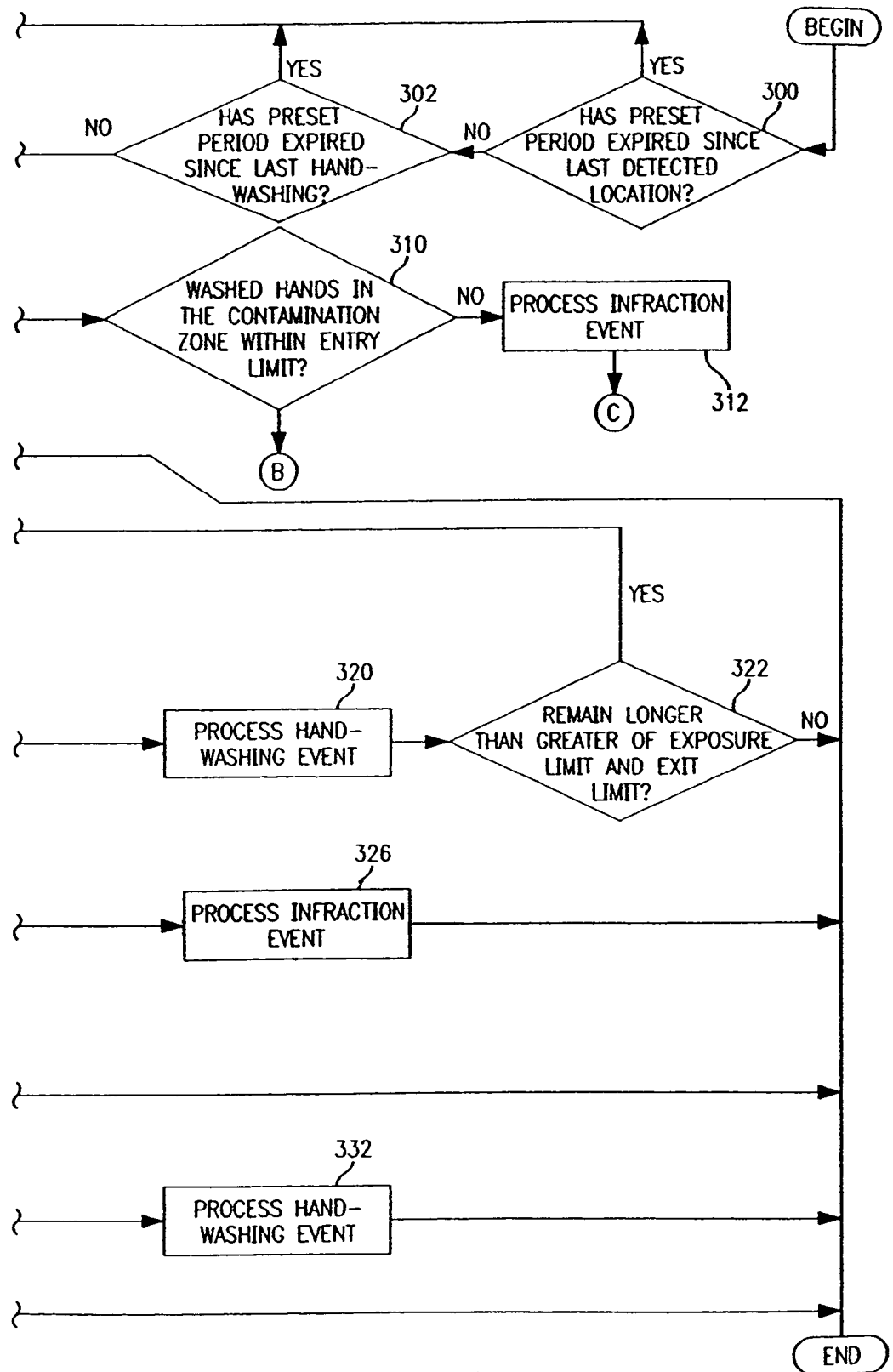

Referring now to FIG. 8, there is illustrated a flowchart of second exemplary handwashing logic which may be implemented by the hygiene monitoring system 100. The second exemplary handwashing logic of FIG. 8 is essentially an alternative to the first exemplary handwashing logic of FIG. 6. In the exemplary embodiment, the master station 129 includes software which when executed by the master station 129 causes the hygiene monitoring system 100 to implement the second exemplary handwashing logic as depicted in FIG. 8. However, while the exemplary embodiment of the hygiene monitoring system 100 implements the handwashing logic of FIG. 8 with software executed by the master station 129, the handwashing logic of FIG. 8 may alternatively be implemented with hardware incorporated in a central device such as the master station 129 or distributed amongst the other components of the hygiene monitoring system 100. Furthermore, the software can be implemented as a stand alone program or can be integrated into the software of an existing system for locating and tracking persons in a facility.

In general, the master station 129 in accord with the alternative handwashing logic of FIG. 8 determines whether various events have occurred based upon information (e.g. caregiver location, handwashing information) received from the various sensors of the hygiene monitoring system 100. Events are points in time at which some change in status may take place. Typically, events are caused by movement of persons into or out of a zone, or the expiration of a time limit for a person in a given zone, or by other mechanisms. In an exemplary embodiment, the master station 129 determines that a caregiver 110 has moved between two zones when the badge 112 worn by the caregiver 110 is detected in the first zone, the badge 112 is later detected in the second zone, and the badge 112 ceases to be detected in the first zone.

In an exemplary embodiment, the master station 129 determines that a controlled Handwash Event has occurred when a caregiver 110 wearing a badge 112 has successfully completed a handwashing at a monitored handwashing device such as sink 102. (See, steps 320, 328, and 332). Moreover, the master station 129 further updates a Contamination Status associated with the caregiver 110 to indicate that the caregiver 110 is "Not Contaminated" whenever the caregiver 110 wearing a badge 112 has completed a successful handwashing, updates and Infraction Status associated with the caregiver 110 to indicates that the caregiver 110 is "Compliant", and if the caregiver was contaminated prior to the controlled Handwashing Event updates the compliance rating for the caregiver. For example, a successful handwashing occurs when the badge 112 worn by the caregiver 110 is detected by a sensor 108 associated with sink 102 for a duration greater than or equal to a preset amount for a successful handwashing. It is within the scope of the invention to require additional parameters to be satisfied for a handwashing to be successful, such as soap was dispensed, drying unit or towel was detected.

The master station 129 of the exemplary embodiment also determines that an Exposure Event has occurred when a caregiver 110 wearing a badge 112 has been in a contamination zone for longer than a Exposure Time associated with that contamination zone. The Exposure Time is the amount of time for a particular contamination zone, that a caregiver 110 can remain in a particular contamination zone without causing an Exposure Event. (See, 314 and 316). However, the master station 129 may also determine that an Exposure Event has occurred when the hygiene monitoring system 100 has not detected a caregiver 110 wearing a badge 112 for more than an hour or some other preset amount of time. (See, steps 300 and 304). Further, the master station 129 may also determine that an Exposure Event has occurred when the master station 129 determines that more than thirty minutes or some other preset amount of time has past since a controlled Handwashing Event has been associated with the caregiver 110 (i.e. the caregiver 110 has not successfully washed her hands for more than some preset amount of time). (See, steps 302 and 304).

In the exemplary embodiment, the Exposure Time is independently defined for each contamination zone of the facility and is typically defined at a constant value for a particular contamination zone. However, the Exposure Time for a particular contamination zone may alternatively be defined based upon a particular caregiver or class of caregivers. For example, the Exposure Time for a particular contamination zone may be defined to cause an Exposure Event for a first caregiver if the first caregiver remains in the contamination zone for ten seconds and cause an Exposure Event for the second caregiver only if the second caregiver remains in the contamination zone for at least twenty seconds. Moreover, when determining how long a particular caregiver 110 has been exposed to a particular contamination zone, the master station 129 of the exemplary embodiment considers a caregiver 110 to have been continuously exposed to the contamination zone if the badge 112 worn by the caregiver 110 is continuously detected in the same contamination zone, regardless of whether the same badge 112 is detected in other zones as well.

The Exit Time is a preset amount of time associated with a particular contamination zone which defines an amount of time that a caregiver 110 has to exit the particular contamination zone following a controlled Handwashing Event without being re-contaminated by the contamination zone. In general, the Exit Time extends the length of time after a controlled Handwashing Event that a caregiver 110 may remain in the contamination zone without being re-contaminated by the contamination zone. In other words, the master station 129 of the exemplary embodiment determines that an Exposure Event has occurred for a caregiver 110 wearing a badge 112 when the caregiver 110 performs a successful handwashing at a monitored handwashing device within a contamination zone and the caregiver 110 remains in the contamination zone for the duration of the greater between the Exposure Time and the Exit Time. (See, steps 318, 320, 322, and 316). In a high risk contamination zone (e.g. isolation room, waste utility room, public restroom) having an Exposure Time of zero associated therewith, the Exit Time permits a caregiver 110 to perform a successful handwashing within the high risk contamination zone and exit the high risk contamination zone within the Exit Time without causing an Exposure Event despite the fact that the Exposure Time had been exceeded.

Similar to the Exposure Time, the exemplary embodiment defines the Exit Time independently for each contamination zone of the facility and typically defines the Exit Time at a constant value for a particular contamination zone. However, the Exit Time for a particular contamination zone may alternatively be defined based upon a particular caregiver or class of caregivers. For example, the Exit Time for a particular contamination zone may be defined such that the master station 129 determines that an Exposure Event has occurred for a first caregiver of a first class of caregivers (e.g. nurses) if the first caregiver does not exit the contamination zone within ten seconds of the controlled Handwashing Event and determines an Exposure Event has occurred for a second caregiver of a second class of caregivers (e.g. physicians) only if the second caregiver does not exit the contamination zone within twenty seconds of the controlled Handwashing Event.

In an exemplary embodiment, the master station 129 determines that an Infraction Event has occurred when a caregiver 110 has committed a violation of the handwashing standards. In the exemplary embodiment, the master station 129 determines whether an Infraction Event has occurred based upon information (e.g. caregiver location, handwashing information) received from the various sensors of the hygiene monitoring system 100. In an exemplary embodiment, the master station 129 utilizes the following rules to determine whether an Infraction Event has occurred.

1) An Infraction Event occurs each time a caregiver 110 exits a contamination zone while "Contaminated", and then does not successfully wash her hands within a Trigger Time of exiting the contamination zone.

2) An Infraction Event occurs each time a caregiver 110 while "Contaminated" enters a contamination zone, and then does not successfully wash her hands within a Entry Time of entering the contamination zone.

The exemplary embodiment defines the Trigger Time as the time for a particular contamination zone that a contaminated caregiver 110 may leave that particular contamination zone without successfully washing the hands at a monitored handwashing device (i.e. cause a controlled Handwashing Event) and not generate an Infraction Event. The exemplary embodiment further defines the Entry Time as the time for a particular contamination zone that a contaminated caregiver 110 may remain in that particular contamination zone without successfully washing her hands at a monitored handwashing device (i.e. cause a controlled Handwashing Event) and not generate an Infraction Event. Similar to the Exposure Time, the Trigger Time and the Entry Time of the exemplary embodiment are independently defined for each contamination zone of the facility and are typically defined at a constant value for a particular contamination zone. The Trigger Time and Entry Time, however, may alternatively be defined based upon a particular caregiver or class of caregivers. For example, the Trigger Time for a particular contamination zone may be defined such that the master station 129 determines that an Infraction Event has occurred for a first caregiver if the first caregiver does not successfully wash her hands (i.e. generate a controlled Handwashing Event) within ten seconds of exiting the contamination zone and cause an Infraction Event for a second caregiver only if the second caregiver does not successfully wash her hands (i.e. generate a controlled Handwashing Event) within twenty seconds of exiting the contamination zone.

The following scenario of events is provided in order to provide further insight into how the second handwashing logic of FIG. 8 may be utilized. For example, in response to a caregiver entering the facility for the first time as a new shift begins, the exemplary hygiene monitoring system 100 would likely determine that either a preset period of time has past since the caregiver was last detected (step 300) or would determine that a preset period of time has past since the last successful handwashing was detected (step 302) and thus process an Exposure Event (step 304). The hygiene monitoring system 100 in processing the Exposure Event generally updates information associated with the caregiver by storing the identification code (i.e. ID) of the caregiver received from the caregiver's badge 112, storing the time the hygiene monitoring system 100 detected the Exposure Event, and updating the contamination status for the caregiver to "Contaminated". Moreover, the hygiene monitoring system 100 in processing the Exposure Event provides the caregiver with an indication of the contamination status associated with the caregiver by, for example, causing the badge 112 to blink yellow.

In response to the badge 112 indicating that the caregiver is contaminated, the caregiver may then stop at a sink 102 located in a non-contamination zone and successfully wash her hands, thus causing a controlled Handwashing Event. Accordingly, the hygiene monitoring system 100 detects the controlled Handwashing Event in the non-contamination zone (step 330) and process the controlled Handwashing Event (step 332). In particular, the hygiene monitoring system 100 in processing the controlled Handwashing Event updates information associated with the caregiver by recording the ID of the caregiver, recording the time the hygiene monitoring system 100 detected the controlled Handwashing Event, recording the ID of the sink 102 at which the caregiver washed her hands, updating a contamination status for the caregiver to "Not Contaminated", updating an infraction status for the caregiver to "Compliant", and if the caregiver was contaminated prior to the controlled Handwashing Event updating the compliance rating for the caregiver. By only updating the compliance rating if the caregiver was contaminated, the hygiene monitoring system 100 prevents caregivers from artificially inflating their compliance rating by performing unnecessary handwashings. Moreover, the hygiene monitoring system 100 in processing the controlled Handwashing Event further provides the caregiver with an indication of her status by, for example, causing the badge 112 to stop blinking, causing the sink 102 to display a "Handwashing Confirmed" message, and causing the sink 102 to display the ID and current compliance rating for the caregiver.

The caregiver after successfully washing her hands may enter patient room A and remain in patient room A for a period of time greater than the Exposure Time associated with patient room A, thus causing an Exposure Event. Accordingly, the hygiene monitoring system 100 detects the Exposure Event (step 314) and processes the Exposure Event (step 316). The hygiene monitoring system 100 in processing the Exposure Event generally updates information associated with the caregiver by storing the ID of the caregiver, storing the time the hygiene monitoring system 100 detected the Exposure Event, storing the location at which contamination occurred, and updating the contamination status associated with the caregiver to "Contaminated". Moreover, the hygiene monitoring system 100 in processing the Exposure Event provides the caregiver with an indication that her status is "Contaminated" by, for example, causing the badge 112 to blink yellow.

The caregiver may then leave patient room A enter a hallway and travel down the hallway for a period of time that is greater than the Trigger Limit for patient room A, thus causing an Infraction Event. The hygiene monitoring system 100 detects the Infraction Event (step 324) and processes the Infraction Event (326). The hygiene monitoring system 100 in processing the Infraction Event generally updates information associated with the caregiver by storing the ID of the caregiver, storing the time the hygiene monitoring system 100 detected the Infraction Event, updating the infraction status of the caregiver to "Infraction Level 1", storing information about the Infraction Event (e.g. did not wash hands within Trigger Time of leaving patient room A), and updating the compliance rating of the caregiver. Further, the hygiene monitoring system 100 provides the caregiver with an indication that her status is "Infraction Level 1" by, for example, causing the badge 112 to slowly blink red.

The caregiver may then enter patient room B and remain in patient room B for a period of time greater than the Entry Limit associated with patient room B without successfully washing her hands, thus causing another Infraction Event. The hygiene monitoring system 100 detects that the caregiver was in a contamination zone (step 306), detects that the caregiver was contaminated (step 308), detects the Infraction Event (step 310) and processes the Infraction Event (step 312). The hygiene monitoring system 100 in processing the Infraction Event generally updates information associated with the caregiver by storing the ID of the caregiver, storing the time the hygiene monitoring system 100 detected the Infraction Event, updating the infraction status of the caregiver to "Infraction Level 2", storing information about the Infraction Event (e.g. did not wash hands within Entry Time of entering patient room B), and updating the compliance rating of the caregiver. Further, the hygiene monitoring system 100 provides the caregiver with an indication that her status is "Infraction Level 2" by, for example, causing the badge 112 to increase its rate of blinking red.

The caregiver may remain in patient room B for a period of time greater than the Exposure Time associated with patient room B, thus causing an Exposure Event. Accordingly, the hygiene monitoring system 100 detects the Exposure Event (step 314) and processes the Exposure Event (step 316). The hygiene monitoring system 100 in processing the Exposure Event generally updates information associated with the caregiver by storing the ID of the caregiver, storing the time the hygiene monitoring system 100 detected the Exposure Event and storing the location at which contamination occurred. Since the caregiver's contamination status is already "Contaminated" the hygiene monitoring system 100 need not update the contamination status to "Contaminated". Moreover, the hygiene monitoring system 100 in processing the Exposure Event continues to provide the caregiver with an indication that her status is "Infraction Level 2" by, for example, continuing to cause the badge 112 to blink red at the increase rate.

The caregiver may then leave patient room B enter a hallway and travel down the hallway for a period of time that is greater than the Trigger Time for patient room B, thus causing another Infraction Event. The hygiene monitoring system 100 detects the Infraction Event (step 324) and process the Infraction Event (326). The hygiene monitoring system 100 in processing the Infraction Event generally updates information associated with the caregiver by storing the ID of the caregiver, storing the time the hygiene monitoring system 100 detected the Infraction Event, updating the infraction status of the caregiver to "Infraction Level 3", storing information about the Infraction Event (e.g. did not wash hands within Trigger Time of leaving patient room B), and updating the compliance rating of the caregiver. Further, the hygiene monitoring system 100 provides the caregiver with an indication that her status is "Infraction Level" by, for example, causing the badge 112 to blink red at an even faster rate than is associated with "Infraction Level 2".

The caregiver may then enter patient room C and remain in patient room C for a period of time greater than the Entry Time associated with patient room C without successfully washing her hands, thus causing another Infraction Event. The hygiene monitoring system 100 detects the Infraction Event (step 310) and processes the Infraction Event (312). The hygiene monitoring system 100 in processing the Infraction Event generally updates information associated with the caregiver by storing the ID of the caregiver, storing the time the hygiene monitoring system 100 detected the Infraction Event, updating the infraction status of the caregiver to "Infraction Level 4", storing information about the Infraction Event (e.g. did not wash hands within Entry Time of entering patient room C), and updating the compliance rating of the caregiver. Further, the hygiene monitoring system 100 provides the caregiver with an indication that her status is "Infraction Level 4" by, for example, causing the badge 112 to be continuously lit red, and causing an audible alarm to be activated whenever the caregiver is in proximity of a handwashing device 101.

In response to noticing the audible alarm and the badge 112 indicating "Infraction Level 4", the caregiver may then stop at a sink 102 located in the patient room C, successfully wash her hands and exit patient room C before the Exit Time has expired, thus causing a controlled Handwashing Event. Accordingly, the hygiene monitoring system 100 detects the controlled Handwashing Event in patient room C (steps 318), processes the controlled Handwashing Event (step 320), and determines that the caregiver exited the patient room C before being recontaminated (step 322). In particular, the hygiene monitoring system 100 in processing the controlled Handwashing Event updates information associated with the caregiver by recording the ID of the caregiver, recording the time the hygiene monitoring system 100 detected the controlled Handwashing Event, recording the ID of the sink 102 at which the caregiver washed her hands, updating the contamination status for the caregiver to "Not Contaminated", updating the infraction status to "Compliant", and if the caregiver was contaminated prior to the controlled Handwashing Event updating the compliance rating for the caregiver. Moreover, the hygiene monitoring system 100 in processing the controlled Handwashing Event further provides the caregiver with an indication of her status by, for example, causing the badge 112 to no longer light on LED causing the sink 102 to display a "Handwashing Confirmed" message, and causing the sink 102 to display the ID and current compliance rating for the caregiver.

The caregiver may then enter a high risk contamination zone (e.g. an isolation room, waste utility room, public restroom) having an Exposure Time of zero, thus causing an Exposure Event. Accordingly, the hygiene monitoring system 100 detects the Exposure Event (step 314) and process the Exposure Event (step 316). The hygiene monitoring system 100 in processing the Exposure Event generally updates information associated with the caregiver by storing the ID of the caregiver, storing the time the hygiene monitoring system 100 detected the Exposure Event and storing the location at which contamination occurred, and updating the contamination status for the caregiver to "Contaminated". Moreover, the hygiene monitoring system 100 in processing the Exposure Event continues to provide the caregiver with an indication that her status is "Contaminated" by, for example, causing the badge 112 to blink yellow.

The caregiver may then exit the high risk contamination zone, re-enter patient room A, and successfully wash her hands before the expiration of the Trigger Time associated with the high risk contamination zone and before the expiration of the Entry Time associated with patient room A. Accordingly, the hygiene monitoring system 100 detects the controlled Handwashing Event in patient room C (step 310 or step 324) and processes the controlled Handwashing Event (step 312 or step 328). In particular, the hygiene monitoring system 100 in processing the controlled Handwashing Event updates information associated with the caregiver by recording the ID of the caregiver, recording the time the hygiene monitoring system 100 detected the controlled Handwashing Event, recording the ID of the sink 102 at which the caregiver washed her hands, updating the contamination status for the caregiver to "Not Contaminated", updating the infraction status for the caregiver to "Compliant", and if the caregiver was contaminated prior to the controlled Handwashing Event updating the compliance rating for the caregiver. Moreover, the hygiene monitoring system 100 in processing the controlled Handwashing Event further provides the caregiver with an indication of her status by, for example, causing the badge 112 to no longer light an LED, causing the sink 102 to display a "Handwashing Confirmed" message, and causing the sink 102 to display the ID and current compliance rating for the caregiver.

Equipment Monitoring

The use of equipment badges 113 and usage sensors 119 on equipment 115 generally allows the hygiene monitoring system 100 to more accurately pinpoint when an event has occurred with a piece of equipment 115 that requires a handwashing. For example, if the hygiene monitoring system 100 determines that (i) a caregiver 110 has entered a patient zone, (ii) the caregiver has remained in the zone for a given length of time, and (iii) the IV pump has been activated during the given length of time, then the hygiene monitoring system 100 can deduce with a high degree of confidence that the caregiver has set an IV line, thus requiring the caregiver to wash her hands before entering the next contamination zone. Accordingly, the handwashing logic of FIG. 6 and the handwashing logic of FIG. 7 may be further modified such that the master station 129 determines whether a caregiver 110 needs to wash her hands based upon a caregiver's likely usage of equipment 115.

Furthermore, the use of equipment badges 113 on equipment 115 enables the hygiene monitoring system 100 to monitor compliancy with hygiene standards defined for the equipment 115. In particular, much of the support equipment 115 within a patient room is electronic and requires special handling when cleaning between patient. The standard practice within most hospitals is that housekeeping is not allowed to clean these devices and the responsibility of such cleaning falls upon the nurse. Since this support equipment 115 commonly comes into direct contact with very sick patients with potentially transferable diseases, such equipment 115 must be decontaminated (or cleaned) before used with another patient.

Figure 9:
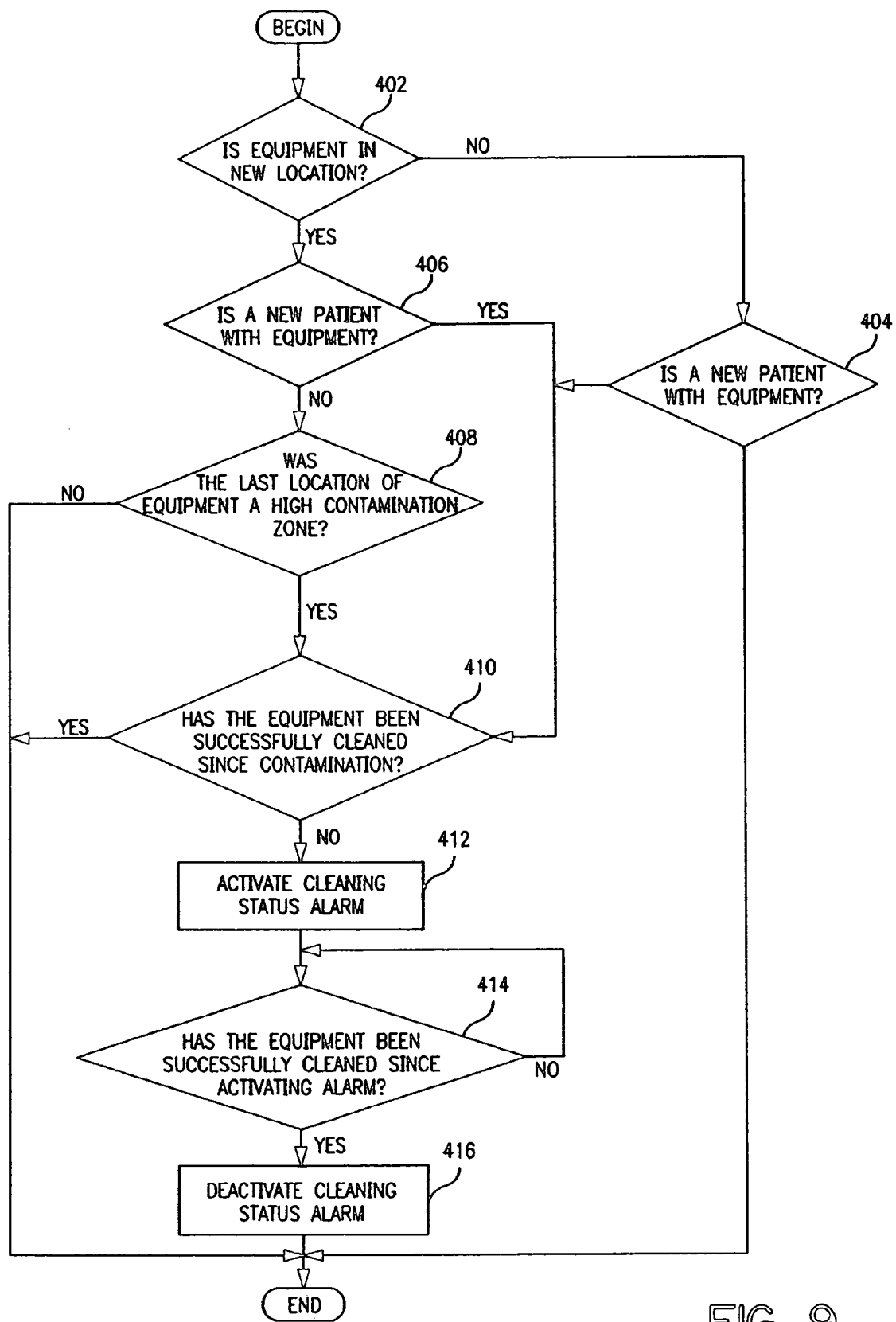
FIG. 9 shows a flowchart representation of equipment decontamination logic which may be used by the hygiene monitoring system.

Referring to FIG. 9, there is depicted a flowchart of exemplary equipment decontamination logic utilized by the exemplary hygiene monitoring system 100. In general, the master station 129 executes the procedure depicted in FIG. 9 whenever equipment 115 having an equipment badge 113 is moved from one location to another location or whenever a new patient is admitted to a patient room containing monitored equipment 115.

As illustrated in FIG. 9, the master station 129 in step 402 determines whether a piece of equipment 115 having an equipment badge 113 is in a new location. The master station 129 in the exemplary embodiment makes this determination by processing location information for the equipment 115 which the master station 129 has received via the equipment badge 113 and the sensors 118 of the hygiene monitoring system 100. If the location information for the equipment 115 indicates that the current location of the equipment 115 is the same as the last location for the equipment 115 (e.g. the current location and the last location of the equipment 115 are the same patient room), then the master station 129 in step 402 determines that the equipment 115 is not in a new location and proceeds to step 404 in order to determine whether a new patient is with the equipment 115. However, if the location information for the equipment 115 indicates that the current location of the equipment 115 is not the same as the last location of the equipment 115 (e.g. the current location of equipment 115 is a first patient room and the last location of the equipment 115 was a different patient room), then the master station 129 proceeds to step 406 in order to determine whether a new patient is with the equipment 115.

In step 404, the master station 129 of the exemplary embodiment determines whether a new patient is with the equipment 115 by comparing patient location information received via badges 112 with equipment location information received via equipment badges 113. If the master station 129 determines based upon the patient location information and the equipment information that a new patient is with the equipment 115 (e.g. the equipment location information indicates the equipment 115 is in a first patient room and the patient location information indicates that a patient who has not previously been detected in the first patient room in now in the first patient room), then the master station 129 determines that a new patient is with the equipment 115 and proceeds to step 410 to confirm whether the equipment 115 has been cleaned. On the other hand, if the master station 129 determines based upon the patient location information and the equipment information that a new patient is not with the equipment 115 (e.g. the equipment location information indicates the equipment 115 is in a first patient room and the patient location information indicates that the patient who is in the first patient has been previously detected in the patient room), then the master station 129 determines that a new patient is not with the equipment 115 and stops execution of the equipment decontamination logic until the next triggering event.

Similarly, the master station 129 of the exemplary embodiment in step 406 determines whether a new patient is with the equipment 115 by comparing patient location information received via badges 112 with equipment location information received via equipment badges 113. If the master station 129 determines based upon the patient location information and the equipment information that a new patient is with the equipment 115 (e.g. the equipment location information and the patient location information indicate that the equipment 115 and the patient have not previously been in the same patient room at the same time), then the master station 129 determines that a new patient is with the equipment 115 and proceeds to step 410 to confirm whether the equipment 115 has been cleaned. On the other hand, if the master station 129 determines based upon the patient location information and the equipment information that a new patient is not with the equipment 115 (e.g. the equipment location information and the patient location information indicate that the equipment 115 and the patient have previously been in the same patient room at the same time), then the master station 129 determines that a new patient is not with the equipment 115 and proceeds to step 408.

In step 408, the master station 129 determines whether the equipment 115 needed to be cleaned due to exposure to a high risk contamination zone such as an isolation room or a waste utility room. To this end, the master station 129 of the exemplary embodiment determines that the equipment 115 needed to be cleaned and proceeds to step 410 if equipment location information for the equipment 115 indicates that the previous location of the equipment 115 was a high risk contamination zone. Otherwise, the master station 129 stops execution of the equipment decontamination logic until the next triggering event.

The master station 129 in step 410 determines whether the equipment 115 has been successfully cleaned since the equipment 115 was last used by another patient or was last exposed to a high risk contamination zone. To this end, the master station 129 determines based upon caregiver and patient location information received from the badges 112, equipment location information received from the equipment badges 113, and cleaning information received from the cleaning sensor 121 whether the equipment 115 has been successfully cleaned since last being contaminated. In particular, the master station 129 determines when the equipment 115 was last contaminated by the equipment's most recent exposure to either another patient or a high risk contamination zone by analyzing received equipment location information and patient location information. Further, the master station 129 determines whether the equipment 115 has been successfully cleaned since the equipment's last exposure to either another patient or a high risk contamination zone by analyzing cleaning information received from the associated cleaning sensor 121. In the exemplary embodiment, the master station 129 and/or the cleaning sensor 121 enforces adequate cleaning of the equipment 115 by requiring that (i) the person cleaning the equipment 115 be in close proximity to the equipment 115 for at least a minimum cleaning period of time, (ii) the cleaning sensor 121 detect moisture associated with the cleaning process for at least the minimum cleaning period of time, and/or (iii) the cleaning sensor 121 detect physical contact associated with the cleaning process for at least the minimum cleaning period of time.

If the master station 129 in step 410 determines that the equipment 115 has been successfully cleaned, then the master station 129 stops execution of the equipment decontamination logic until the next triggering event. However, if the master station 129 in step 410 determines that the equipment 115 has not been successfully cleaned, then the master station 129 in step 412 activates a cleaning status alarm associated with the equipment 115 and records the fact that the patient has been exposed to a contaminated piece of equipment 115. As a result of activating the cleaning status alarm, an indication is provided that the equipment 115 needs to be cleaned. For example, lights on the equipment 115 itself and/or a status monitor for the patient room may be illuminated. Also, sound may be emitted from the equipment 115 and/or a status monitor for the patient room.

Similar to step 410, the master station 129 in step 414 determines whether the equipment 115 has been successfully cleaned since the activation of the cleaning status alarm. To this end, the master station 129 determines based upon caregiver and patient location information received from the badges 112, equipment location information received from the equipment badges 113, and cleaning information received from the cleaning sensor 121 whether the equipment 115 has been successfully cleaned. In particular, the master station 129 analyzes the information received from badges 112, 113, and the associated cleaning sensor 121 in order to determine whether (i) the person cleaning the equipment 115 has been in close proximity to the equipment 115 for at least a minimum cleaning period of time, (ii) the cleaning sensor 121 has detected moisture associated with the cleaning process for at least the minimum cleaning period of time, and/or (iii) the cleaning sensor 121 has detected physical contact associated with the cleaning process for at least the minimum cleaning period of time.

If the master station 129 in step 414 determines that the equipment 115 has not been successfully cleaned, then the master station 129 returns to step 412 to make another determination of whether the equipment 115 has been successfully cleaned. If the master station 129 in step 414 determines that the equipment 115 has been successfully cleaned, then the master station 129 in step 416 deactivates the cleaning status alarm which was activated in step 412 and records the fact that the equipment 115 has been successfully cleaned.

The following scenario illustrates the operation of the hygiene monitoring system 100 in implementing the equipment decontamination logic of FIG. 9. To begin, a first patient who is wearing an ID wristband equipped with a badge 112 is admitted to a patient room. Later, a clean IV pump that is equipped with an equipment badge 113 and cleaning sensors 121 is brought into the patient room. As a result, the master station 129 would determine that the equipment 115 has changed location (step 402) and a new patient is with the equipment 115 (step 406). The master station 129 then would determine in step 410 that the equipment 115 has been cleaned since its last use or exposure to a high risk contamination zone. Accordingly, the master station 129 would exit the procedure without activating the cleaning status alarm.

After two days, the patient is transferred from his patient room in the intensive care unit (ICU) to another room of the surgery floor. The IV pump accompanies the patient during the transfer to the new room. Accordingly, the master station 129 would determine that the equipment 115 has changed location (step 402) but that a new patient is not with the equipment 115 (step 406). The master station 129 then would determine in step 408 that the equipment 115 has been not been contaminated due to exposure to a high risk contamination zone. Therefore, the master station 129 would exit the procedure without activating the cleaning status alarm.

In another day, the first patient is discharged from the hospital and the IV pump is returned to the ICU floor and placed into the original patient room with a new patient who is wearing an ID wristband equipped with a badge 112. At this point, the master station 129 would determine that the equipment 115 has changed location (step 402) and that a new patient is with the equipment 115 (step 406). The master station 129 then would determine in step 410 that the equipment 115 has been not been cleaned since being contaminated due to being exposed to the discharged first patient. Accordingly, the master station 129 in step 412 would activate the cleaning status alarm associated with the IV pump and record the fact that the IV pump was not cleaned before being placed in the room with the new patient. The master station 129 would then continually monitor the IV pump until the cleaning sensors 121 indicate that the IV pump has been properly cleaned (step 414). At which time, the master station 129 would deactivate the cleaning status alarm associated with the IV pump and record the fact that the IV pump has been properly cleaned (step 416).

Compliance Reports and System Interface

Shown in FIGS. 4, 10–12, 13A, 13B, and 14 are various examples of different compliance reports 128 that are generated by the hygiene monitoring system 100. While the exemplary compliance reports 128 only depict compliance information associated with handwashing, the compliance reports 128 could easily be modified or new compliance reports created which depict compliance information associate with proper equipment cleaning practices. In one embodiment, hygiene compliance is analyzed using chi-squared analysis. In another embodiment, hygiene compliance compares handwashing events to employee movement. In another embodiment, every Event that affects the Contamination Status, Infraction Status, Compliance Rating, or Maintenance Status as well as every change in location for a badge 112, 113 is reported to the master station 129. Such information is sent to the master station 129 in the form of messages. Exemplary messages are presented in Table 1.

TABLE 1

| Message | When | Data |
| --- | --- | --- |
| Location Entry | Transmitted when a badge is first seen in a location. | Badge ID Sensor ID Timestamp |
| Location Exit | Transmitted when a badge is no longer seen by a sensor. | Badge IID Sensor ID Timestamp |
| Contamination Event | Transmitted when a Badge ID's status changes from "not contaminated" to "contaminated". | Badge ID Sensor ID Timestamp |
| Infraction Event | Transmitted each time an event affecting an individual's compliance rating occurs. | Badge ID Sensor ID Timestamp Infraction Level |
| Controlled Handwash Event | Transmitted when a Controlled Handwash Event has been completed. | Badge ID Sensor ID Timestamp |
| Failed Handwash Event | Transmitted when a Failed Handwash Event has occurred. | Badge ID Sensor ID Timestamp |
| Maintenance Request Event | Transmitted when the status bits of a particular faucet monitoring device indicate that a Maintenance Activity is required. | Sensor ID Timestamp Maintenance Activity |

FIG. 10 shows a hospital summary report. The hospital summary report provides a summary of compliance to handwashing guidelines for the hospital as a whole and specific departments within a healthcare environment. The purpose of the report is to identify departments within the hospital that have the most difficulty with compliance so that corrective action may be taken. As can be seen in FIG. 10, the report provides the time period that this report is associated with, an overall compliance rating and a breakdown of compliance ratings based upon department. As shown in FIG. 10, department ICU had a 70 percent compliance for a total number of 1500 visitations during the time period of October 1999.

In FIG. 11, a department summary report is shown. The department summary report provides a summary of the compliance to handwashing guidelines for a specific department within a healthcare environment. The purpose of the report is to identify areas within the unit and groups of caregivers which have the most difficulty with compliance so that corrective action may be taken. As shown in FIG. 11, the department summary report includes the department name and number, the time period for which the report is generated and an overall department compliance rating. The report also breaks the department down into different locations or zones. These are provided with a specific identification number (e.g. location 201). This breakdown allows the person viewing the report to determine which zones are having the most difficulty with handwashing compliance. Also shown in FIG. 11, is the compliance for each zone along with the number of visitations to that zone during a specific time period. The department summary report also provides a breakdown for the groups within the report showing the individual groups compliance ratings. This breakdown allows quick identification of the contribution made by each group to the overall compliance rating.

FIG. 12 illustrates an example of a group summary report. The group summary report provides a summary of the compliance to handwashing guidelines for a specific group of caregivers within the healthcare environment. The purpose of the report is to identify areas within the unit where the compliance is low so that corrective action may be taken within a specific group of caregivers. As can be seen from FIG. 12, the visiting physician group summary report contains the department name and number, the time period of the report and the overall compliance rating of the report. The report breaks the department down into different locations or zones. This breakdown allows the person reviewing the report to determine which zones are having the most difficulty with handwashing compliance. The report also breaks down the group into the individuals within the group showing their identification number, name, number of visitations and the individual compliance. This allows identification of the contribution of each individual to the overall compliance rating of the group.

FIG. 13A shows an individual summary report. The individual summary report provides a summary of the compliance to handwashing guidelines for a specific individual within a healthcare environment. The purpose of the report is to identify areas within the unit wherein an individual is having the most difficulty with compliance so that corrective action may be taken. As shown in FIG. 13A, the individual summary report includes the identification number of the person, the name of the person, the department and group to which the person belongs, the time period for the report, and the compliance rating for the department. Also provided are the different locations or zones within the department with the number of visitations the particular individual made to those zones, and the individual's compliance rating during those visits.

FIG. 13B shows a detailed compliance report for an individual. The detailed compliance report provides a summary of the compliance to handwashing guidelines for a specific individual over a specific time period within the healthcare environment. The purpose of the report is to understand traffic patterns of the individual so that greater insight as to why compliance is not occurring may be gained. As shown in FIG. 13B, the identification number of the individual, the name of the individual, the department and group to which the individual belongs, the time period for which the report is being generated, and the compliance rating for the individual are shown. The lower portion of the report breaks down the locations or zones the individual visited along with the times of the visits and the status that was recorded by the handwashing monitoring logic.

Figure 14:
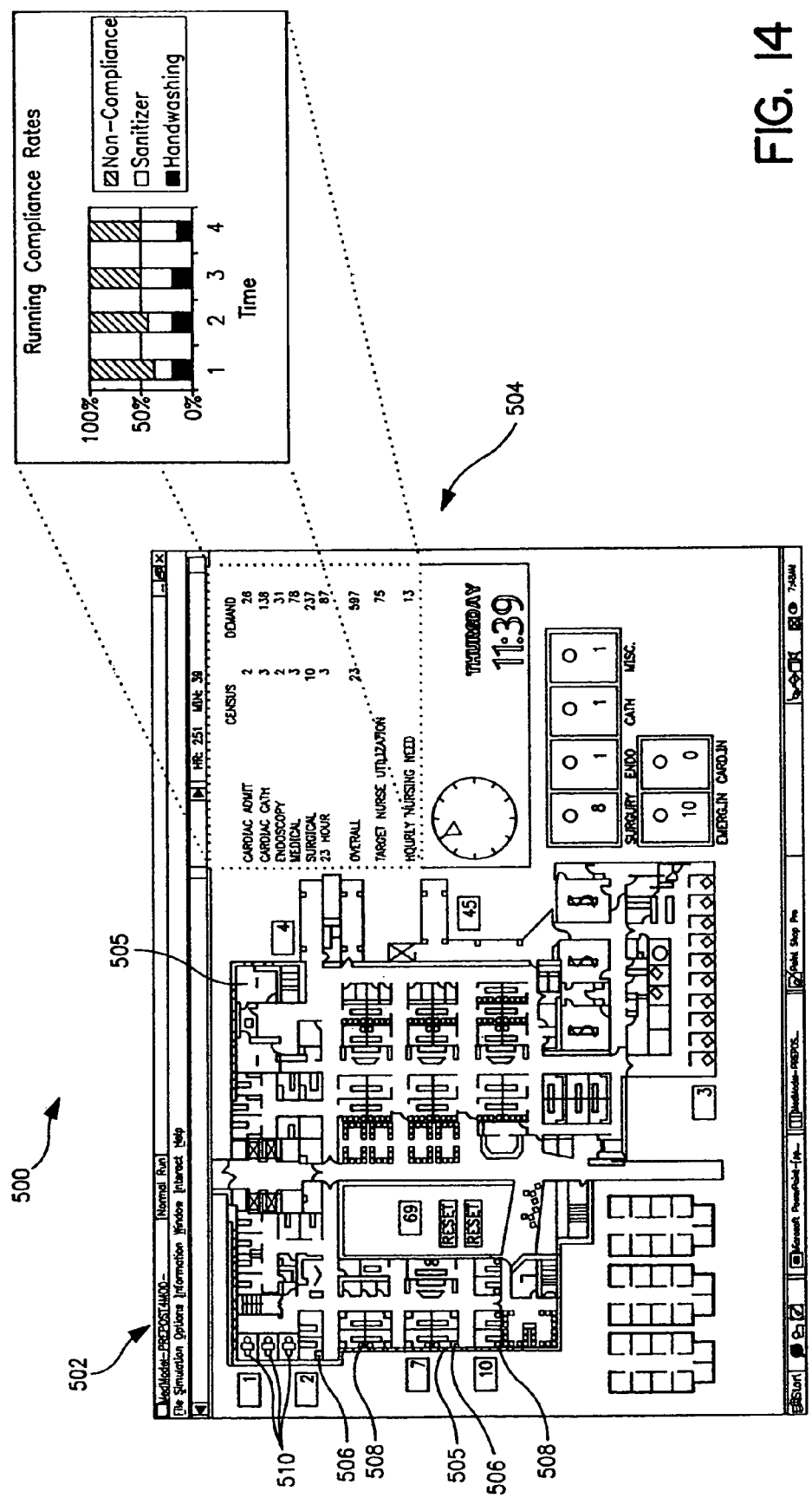
FIG. 14 shows an exemplary user interface of the hygiene monitoring system.

FIG. 14 shows an exemplary user interface 500 of the hygiene monitoring system 100. In the exemplary embodiment, the user interface was implemented as a MedModel application executing on the master station 129. As is known to those skilled in the art, MedModel is a software tool of ProModel Corporation which is generally used for simulation modeling of healthcare facilities. As depicted, the user interface 500 generally includes a floor layout 502 and a scoreboard status 505. The floor layout 502 generally depicts the zones and rooms 504 of the facility as well as handwashing devices 506, equipment 508, and persons 510. In the exemplary embodiment, the zones and rooms 504 are color coded in order to enable a user to quickly identify the classification of the zones and the room 504. Moreover, the handwashing devices 506 are depicted such that they blink if there is a problem associated with the handwashing device (e.g. out of soap). Moreover, equipment 508 and persons 510 are also color coded in order to depict their current status (e.g. contaminated, or not contaminated).

The scoreboard status 504 generally provides pseudo-realtime statistics and other information for the facility. For example, as depicted in FIG. 14, the scoreboard status 504 may provide a display of running compliance rates in regard to a defined handwashing policy for the facility. In particular, the scoreboard status 504 may be set to display overall and unit compliance ratings and contribution of sanitizer and handwashing events over the past hour, day, month and year.

The user interface 500 also enables a user to view or modify status details based upon a clearance level associated with the particular user. In the exemplary embodiment, a user may have a first clearance level, a second clearance level, or a third clearance level associated therewith. If a first clearance level is associated with the user, then the exemplary user interface 500 enables a user to select a given room 505 in order to view the classification of the room, status of sensors in the room, and overall compliance associated with the room. A user having a second clearance level may do all of the above with respect to rooms 505 plus the user may respond to maintenance alarms and change room classifications via the user interface 500. Further, a user having a third clearance level may do all of the above with respect to rooms 505 plus the user may reconfigure room layout and sink locations, reassign sensor classifications (e.g. associated with or not associated with a handwashing device), change color layout, view managerial reports such as running compliance rates and employee compliance rates.

If a user has the first clearance level, then that user may also select a sink 506 in order to obtain system status information for the sink, obtain a graphic display of soap level and scrub duration setting, obtain a graphic display of the unit use profile for the past day, month or year compared to the average and overall use of all other sinks, obtain information comparing completed versus failed controlled handwashing events for the sink, and obtain a graphical display of mechanical performance rating for the sink. If a user has the second or third clearance level, then that user may perform all of the above actions in regard to sinks 506 plus the user may respond to maintenance alarms associated with the sinks.

If a user has the first clearance level, then that user may also select a hand sanitizer 506 in order to obtain system status information for the hand sanitizer, obtain a graphic display of sanitizer level and scrub duration setting, obtain a graphic display of the unit use profile for the past day, month or year compared to the average and overall use of all other sinks, and obtain information comparing completed versus failed controlled handwashing events for the hand sanitizer, and obtain a graphical display of mechanical performance rating for the hand sanitizer. If a user has the second or third clearance level, then that user may perform all of the above actions in regard to hand sanitizers 506 plus the user may respond to maintenance alarms associated with the hand sanitizers.

If a user has the third clearance level, then that user may further select a person 510 to display the ID number of individual, obtain a graphical display of the individuals compliance and the individuals contribution of sanitizer and handwashing events for the past day, month or year compared to average and overall compliance rating, obtain distribution of infraction levels for the individual, and obtain an employee profile for the individual including name, number, title, unit etc.

If a user has the first clearance level, then that user may further select equipment 508 to display a description of the equipment, display the current status of the equipment, obtain a graphic display of the cleaning profile for the past day, month or year compared to average and overall cleaning of all other devices, and obtain a graphical display on overall compliance to cleaning for the equipment. If a user has the second clearance level, then that user may perform all of the above in regard to equipment 508 plus the user may respond to maintenance alarms associated with the equipment. If a user has the third clearance level, then that user may perform all of the above in regard to equipment 508 plus the user may reclassify the ID associated with the equipment.

It is within the scope of the present invention for the same overall system to be used for a multitude of applications. As already stated the system can be used to monitor handwashing compliance, monitoring device activity, equipment tracking, and visitor tracking. By utilizing the same backbone infrastructure the cost for the entire system is able to be spread across a multitude of applications. Additionally the cost of adding additional modules such as visitor tracking is minimal because the backbone infrastructure is already in place.

The invention claimed is:

1. A method of monitoring hygiene compliance, comprising:
    determining whether a person has encountered a monitored piece of moveable equipment; and
    updating status information associated with the person to indicate that the person is contaminated in response to the determining step determining that the person has encountered the monitored piece of moveable equipment.

2. The method of claim 1, wherein the monitored piece of moveable equipment is associated with being contaminated.

3. The method of claim 1, further comprising
    determining whether the person has utilized a decontamination station; and
    updating status information associated with the person to indicate that the person is decontaminated in response to determining that the person has utilized the decontamination station.

4. A method of monitoring hygiene compliance, comprising the steps of:
   monitoring a person;
   monitoring an object;
   associating a status with the person, the status being one of contaminated and non-contaminated; and
   associating a status with the object, the status being one of contaminated and non-contaminated; the status of the object being switchable between contaminated and non-contaminated.

5. The method of claim 4, further comprising establishing at least one contamination zone, wherein the person is associated with a status of contaminated if the person enters a contamination zone.

6. The method of claim 4, further comprising establishing at least one contamination zone, wherein the object is associated with a status of contaminated if the object enters a contamination zone.

7. The method of claim 4, wherein the person is associated with a status of contaminated when the person encounters an object associated with a status of contaminated.

8. The method of claim 4, wherein the object is associated with a status of contaminated when the object encounters a person associated with a status of contaminated.

9. The method of claim 4, wherein the person is associated with a status of non-contaminated when the person encounters a decontamination device, and the object is associated with a status of not contaminated when the object encounters a decontamination device.

10. The method of claim 9, wherein the person is considered to have encountered the decontamination device whenever that person is proximate the decontamination device.

11. The method of claim 9, wherein the person is considered to have encountered the decontamination device whenever that person is proximate the decontamination device and the decontamination device is activated.

12. A method of monitoring hygiene compliance, comprising the steps of:
   monitoring a non-person object;
   establishing at least one contamination zone; and
   updating status information associated with the non-person object to indicate that the non-person object is contaminated in response to the monitoring step determining that the non-person object is in a contamination zone.

13. A method of monitoring hygiene compliance, comprising the steps of:
   monitoring an object;
   establishing at least one contamination zone;
   updating status information associated with the object to indicate that the inanimate object is contaminated in response to the monitoring step determining that the object is in a contamination zone; and
   updating status information associated with the object to indicate that the object is contaminated in response to the monitoring step determining that the object has encountered a person who is associated with a status of contaminated.

14. The method of claim 12, further including the step of updating status information associated with the non-person object to indicate that the non-person object is contaminated in response to the monitoring step determining that the non-person object has encountered a another object that is associated with being contaminated.

15. A method of monitoring hygiene compliance for a plurality of items including at least one of persons and objects, the method comprising:
   tracking a first item;
   establishing at least one contamination zone;
   updating status information associated with the first item if the first item enters a contamination zone such that the first item is associated with being contaminated;
   updating status information associated with a second item if the second item enters a zone proximate the first item that is associated with being contaminated such that the second item is associated with being contaminated; and
   updating status information associated with the first item when the first item is subjected to a decontamination process such that the first item is associated with being non-contaminated.

16. The method of claim 15, wherein a violation is logged when one of the first and second items having a status of contaminated enters a contamination zone.

17. The method of claim 15, wherein when the first item is associated with being contaminated as a result of entering a particular contamination zone, the contamination of the first item is associated with the particular contamination zone that is a source of the contamination of the item.

18. The method of claim 17, wherein when the second item is contaminated by the first item, the second item is also associated with the particular contamination zone that was the source of the contamination of the first item.

19. The method of claim 17, wherein when a contaminated item reenters the particular contamination zone that is associated with the contaminated item as the only source of contamination of the item, a violation fails to be logged.

20. The method of claim 17, wherein when a contaminated first item becomes proximate a contaminated second item, the second item being associated with a different contamination zone than the contamination zone associated with the first item, both the first and second items are noted as being doubly contaminated and associated with two contamination zones.

21. A method of monitoring hygiene compliance for a plurality of items including at least one of persons and objects, the method comprising:
   tracking a first item;
   tracking a second item;
   assigning a status to the first item indicating whether the first item is one of contaminated and non-contaminated; and
   assigning a status to the second item indicating whether the second item is one of contaminated and non-contaminated, wherein if the first item encounters the second item and one of the first and second items is assigned a status of contaminated, then the other of the first and second items is also assigned a status of contaminated.

22. The method of claim 21, wherein the first item is considered to have encountered the second item when the two items are within a defined proximity of one another for a defined period of time.

23. The method of claim 21, wherein the second item is a patient.

24. The method of claim 21, wherein if the first item is contaminated before encountering the second item, the encounter causes a violation to be logged.

25. The method of monitoring hygiene compliance in items including at least one of persons and objects including the steps of:

establishing at least one contamination zone;

tracking a plurality of items;

associating a first item with a status of contaminated when the first item enters a contamination zone; and associating a second item with a status of contaminated when the second item encounters the first item and the first item is associated with the status of contaminated during the encounter.

26. The method of claim 25, wherein the first item must stay within the contamination zone for a predetermined period of time before it is associated with the status of contaminated.

27. A method of monitoring hygiene compliance in items including at least one of persons and objects including the steps of:

tracking a plurality of items;

associating a first item with a second item;

associating a third item with the second item; and logging a violation unless the second item is decontaminated before being associated with the third item.

28. The method of claim 27, wherein the first item is a first patient, the second item is an object, and the third item is a second patient.

29. The method of claim 27, wherein the tracking step includes the monitoring of the second item to determine if the second item is subjected to a decontamination process.

30. The method of claim 27, further comprising the step of updating status information associated with the second item to a contaminated status after it is associated with the first item.

* * * * *